(12) United States Patent
Wolpe et al.

(10) Patent No.: US 11,976,298 B2
(45) Date of Patent: May 7, 2024

(54) AUGMENTATION OF CELL THERAPY EFFICACY INCLUDING TREATMENT WITH ALPHA 1,3 FUCOSYLTRANSFERASE

(71) Applicant: Targazyme, Inc., Carlsbad, CA (US)

(72) Inventors: Stephen D. Wolpe, Boyds, MD (US); Leonard Miller, Carlsbad, CA (US); Lynnet Koh, Carlsbad, CA (US); Thomas E. Ichim, San Diego, CA (US)

(73) Assignee: Targazyme, Inc., Carlsbad, CA (US)

( * ) Notice: Subject to any disclaimer, the term of this patent is extended or adjusted under 35 U.S.C. 154(b) by 865 days.

(21) Appl. No.: 16/135,487

(22) Filed: Sep. 19, 2018

(65) Prior Publication Data

US 2019/0017023 A1 Jan. 17, 2019
US 2023/0416681 A9 Dec. 28, 2023

Related U.S. Application Data

(63) Continuation of application No. 15/347,500, filed on Nov. 9, 2016, now abandoned, which is a continuation of application No. 14/182,141, filed on Feb. 17, 2014, now abandoned, which is a continuation-in-part of application No. 12/997,230, filed as application No. PCT/US2009/046800 on Jun. 9, 2009, now abandoned.

(60) Provisional application No. 61/060,084, filed on Jun. 9, 2008.

(51) Int. Cl.
| | |
|---|---|
| *C12N 5/0783* | (2010.01) |
| *A61K 35/17* | (2015.01) |
| *C12N 5/00* | (2006.01) |
| *C12N 5/0775* | (2010.01) |
| *C12N 5/0789* | (2010.01) |
| *C12N 5/0797* | (2010.01) |
| *A61K 35/12* | (2015.01) |

(52) U.S. Cl.
CPC ............ *C12N 5/0638* (2013.01); *A61K 35/17* (2013.01); *C12N 5/0006* (2013.01); *C12N 5/0623* (2013.01); *C12N 5/0637* (2013.01); *C12N 5/0647* (2013.01); *C12N 5/0663* (2013.01); *C12Y 204/01065* (2013.01); *A61K 35/12* (2013.01); *A61K 2035/124* (2013.01); *C12N 2501/70* (2013.01); *C12N 2501/724* (2013.01)

(58) Field of Classification Search
CPC ...... C12N 5/068; C12N 5/006; C12N 5/0623; C12N 5/0637; C12N 5/0647; C12N 5/0663; C12N 2501/70; C12N 2501/724; A61K 35/17; A61K 35/12; A61K 2035/124; C12Y 204/01065; A61P 1/16; A61P 3/10; A61P 9/00; A61P 9/10; A61P 15/00; A61P 19/08; A61P 21/00; A61P 25/00; A61P 25/16; A61P 25/28; A61P 35/00; A61P 37/02
See application file for complete search history.

(56) References Cited

U.S. PATENT DOCUMENTS

| | | |
|---|---|---|
| 6,331,658 B1 | 12/2001 | Cooper et al. |
| 2003/0113303 A1* | 6/2003 | Schwartz .................. A61P 9/10 424/93.21 |
| 2003/0119185 A1* | 6/2003 | Berenson ............. C12N 5/0635 435/372 |
| 2004/0209357 A1 | 10/2004 | Xia et al. |
| 2004/0247574 A1 | 12/2004 | Christopherson, II et al. |
| 2005/0026133 A1 | 2/2005 | Nakatsuji et al. |
| 2005/0048036 A1 | 3/2005 | Hedrick et al. |
| 2005/0196386 A1 | 9/2005 | Blazar et al. |
| 2006/0210558 A1* | 9/2006 | Sackstein ......... C07K 14/70585 424/277.1 |
| 2006/0228340 A1 | 10/2006 | Xia et al. |
| 2007/0190023 A1 | 8/2007 | Battista et al. |
| 2008/0044383 A1 | 2/2008 | Sackstein |
| 2009/0148839 A1 | 6/2009 | Laine et al. |
| 2009/0226404 A1* | 9/2009 | Schuler ................ C12N 5/0636 424/93.21 |
| 2009/0239296 A1 | 9/2009 | Sackstein |
| 2010/0150883 A1 | 6/2010 | Xia et al. |
| 2010/0304436 A1 | 12/2010 | Chen et al. |
| 2010/0311036 A1 | 12/2010 | He |
| 2011/0091434 A1 | 4/2011 | Miller et al. |
| 2011/0097308 A1 | 4/2011 | Xia et al. |
| 2011/0136682 A1 | 6/2011 | Bosques et al. |
| 2013/0058959 A1 | 3/2013 | Sackstein |
| 2013/0251688 A1 | 9/2013 | Xia et al. |
| 2014/0161782 A1 | 6/2014 | Wolpe et al. |
| 2016/0331785 A1 | 11/2016 | Xia et al. |
| 2017/0121673 A1 | 5/2017 | Wolpe |
| 2018/0078583 A1 | 3/2018 | Xia et al. |

FOREIGN PATENT DOCUMENTS

| | | |
|---|---|---|
| WO | 9739104 | 10/1997 |
| WO | 2005017115 A2 | 2/2005 |

(Continued)

OTHER PUBLICATIONS

Cao et al., Am J. Pathol., 169(1):325-336 (2006) (Year: 2006).*
Kalka et al., PNAS, 97(7):3422-3427 (2000) (Year: 2000).*
Oh et al., Blood 110(12):3891-3899 (2007) (Year: 2007).*
Eming, SA et al. Inflammation in wound repair: Molecular and cellular mechanisms. Journal of Investigative Dermatology. Mar. 2007. 127: 514-525. (Year: 2007).*
Davidson, A et al. Autoimmune diseases. The New England Journal of Medicine. 2001. 345(5): 340-350. (Year: 2001).*
Bostrom, EA et al. Non-malignant blood disorders and their impact on oral health: an overview. Current Oral Health Reports. 2019. 6: 161-168. (Year: 2019).*

(Continued)

*Primary Examiner* — David W Berke-Schlessel
*Assistant Examiner* — Susan E. Fernandez
(74) *Attorney, Agent, or Firm* — Dunlap Codding, P.C.

(57) ABSTRACT

Disclosed are methods, compositions of matter, and kits useful for augmentation of cells through modification of cellular membrane properties following ex vivo treatment.

7 Claims, 5 Drawing Sheets
(4 of 5 Drawing Sheet(s) Filed in Color)

(56) References Cited

FOREIGN PATENT DOCUMENTS

| WO | WO-2005017115 A2 * | 2/2005 | ....... C07K 14/70564 |
|----|----|----|----|
| WO | 20091582187 A1 | 6/2009 | |

OTHER PUBLICATIONS

Hassanpour, SH et al. Review of cancer from perspective of molecular. Journal of Cancer Research and Practice. 2017. 4: 127-129. (Year: 2017).*
Bruserud, O et al. Biological treatment in acute myelogenous leukaemia: how should T-cell targeting immunotherapy be combined with intensive chemotherapy? Expert Opin. Biol. Ther. 2001. 1(6): 1005-1016. (Year: 2001).*
International Search Report, dated Sep. 30, 2015, in PCT/EP2015/039370, filed Jul. 7, 2015.
Written Opinion of the International Searching Authority, dated Sep. 30, 2015, in PCT/EP2015/039370, filed Jul. 7, 2015.
U.S. Appl. No. 15/322,565; Stephen D. Wolpe, filed Dec. 28, 2016; Office Action dated Jul. 5, 2017.
U.S. Appl. No. 15/322,565; Stephen D. Wolpe, filed Dec. 28, 2016; Response to Office Action filed Aug. 22, 2017.
U.S. Appl. No. 15/322,565; Stephen D. Wolpe, filed Dec. 28, 2016; Office Action dated Sep. 8, 2017.
Giancola, et al.; "Cell Therapy: cGMP Facilities and Manufacturing," Muscles, Ligaments and Tendons Journal (2012), vol. 2, No. 3, pp. 243-247.
Ayatollahi, et al.; "Conditions to Improve Expansion of Human Mesenchymal Stem Cells Based on Rat Samples," World Journal Stem Cells (2012), vol. 4, No. 1, pp. 1-8.
U.S. Appl. No. 15/347,500; Stephen D. Wolpe, filed Nov. 9, 2016; Office Action dated Aug. 25, 2017.
U.S. Appl. No. 15/347,500; Stephen D. Wolpe, filed Nov. 9, 2016; Response to Office Action filed Feb. 23, 2018.
U.S. Appl. No. 15/347,500; Stephen D. Wolpe, filed Nov. 9, 2016; Final Office Action dated Mar. 19, 2018.
U.S. Appl. No. 10/769,686; Xia, et al.; Office Action dated Apr. 17, 206; filed Jan. 30, 2004.
U.S. Appl. No. 10/769,686; Xia, et al.; Amendment filed Jun. 7, 2006; filed Jan. 30, 2004.
U.S. Appl. No. 10/769,686; Xia, et al.; Office Action dated Aug. 1, 2006; filed Jan. 30, 2004.
U.S. Appl. No. 10/769,686; Xia, et al.; Interview Summary dated Sep. 15, 2006; filed Jan. 30, 2004.
U.S. Appl. No. 10/769,686; Xia, et al.; Amendment filed Sep. 19, 2006; filed Jan. 30, 2004.
U.S. Appl. No. 10/769,686; Xia, et al.; Office Action dated Dec. 22, 2006; filed Jan. 30, 2004.
U.S. Appl. No. 10/769,686; Xia, et al.; Amendment and Response filed Feb. 12, 2007; filed Jan. 30, 2004.
U.S. Appl. No. 10/769,686; Xia, et al.; Notice of Allowance dated May 29, 2007; filed Jan. 30, 2004.
U.S. Appl. No. 11/448,359; Xia, et al.; Preliminary Amendment filed May 5, 2008; filed Jun. 7, 2006.
U.S. Appl. No. 11/448,359; Xia, et al.; Office Action dated Jan. 12, 2009; filed Jun. 7, 2006.
U.S. Appl. No. 11/448,359; Xia, et al.; Amendment and Response to Office Action filed Jul. 15, 2009; filed Jun. 7, 2006.
U.S. Appl. No. 11/448,359; Xia, et al.; Final Office Action dated Dec. 16, 2009; filed Jun. 7, 2006.
U.S. Appl. No. 11/448,359; Xia, et al.; Amendment and Response to Final Office Action filed Feb. 17, 2010; filed Jun. 7, 2006.
U.S. Appl. No. 11/448,359; Xia, et al.; Notice of Allowance dated Mar. 23, 2010; filed Jun. 7, 2006.
U.S. Appl. No. 11/448,359; Xia, et al.; Amendment Under 37 CFR 1.312 filed Jun. 25, 2010; filed Jun. 7, 2006.
U.S. Appl. No. 12/707,481; Xia, et al.; Preliminary Amendment filed Jul. 20, 2010; filed Feb. 17, 2010.
U.S. Appl. No. 12/707,481; Xia, et al.; Office Action dated Aug. 27, 2010; filed Feb. 17, 2010.
U.S. Appl. No. 12/707,481; Xia, et al.; Amendment and Response to Office Action filed Feb. 21, 2011; filed Feb. 17, 2010.
U.S. Appl. No. 12/707,481; Xia, et al.; Final Office Action dated Mar. 28, 2011; filed Feb. 17, 2010.
U.S. Appl. No. 12/707,481; Xia, et al.; Amendment and Response and Request for Continued Examination filed Aug. 12, 2011; filed Feb. 17, 2010.
U.S. Appl. No. 12/707,481; Xia, et al.; Notice of Allowance dated Aug. 24, 2011; filed Feb. 17, 2010.
U.S. Appl. No. 12/707,481; Xia, et al.; Notice of Allowance dated Sep. 9, 2011; filed Feb. 17, 2010.
U.S. Appl. No. 12/948,489; Xia, et al.; Office Action dated Apr. 12, 2012; filed Nov. 17, 2010.
U.S. Appl. No. 12/948,489; Xia, et al.; Amendment and Response to Office Action filed Jul. 12, 2012; filed Nov. 17, 2010.
U.S. Appl. No. 12/948,489; Xia, et al.; Office Action dated Aug. 24, 2012; filed Nov. 17, 2010.
U.S. Appl. No. 12/948,489; Xia, et al.; Amendment and Response to Office Action filed Dec. 21, 2012; filed Nov. 17, 2010.
U.S. Appl. No. 12/948,489; Xia, et al.; Notice of Allowance dated Feb. 12, 2013; filed Nov. 17, 2010.
U.S. Appl. No. 13/894,123; Xia, et al.; Office Action dated Sep. 11, 2014; filed May 14, 2013.
U.S. Appl. No. 13/894,123; Xia, et al.; Response to Office Action filed Mar. 11, 2015; filed May 14, 2013.
U.S. Appl. No. 13/894,123; Xia, et al.; Office Action dated Jun. 22, 2015; filed May 14, 2013.
U.S. Appl. No. 13/894,123; Xia, et al.; Amendment and Response to Office Action filed Oct. 13, 2015; filed May 14, 2013.
U.S. Appl. No. 13/894,123; Xia, et al.; Final Office Action dated Mar. 18, 2016; filed May 14, 2013.
U.S. Appl. No. 13/894,123; Xia, et al.; Response to Final Office Action filed Mar. 22, 2016; filed May 14, 2013.
U.S. Appl. No. 13/894,123; Xia, et al.; Notice of Allowance dated Apr. 12, 2016; filed May 14, 2013.
U.S. Appl. No. 13/894,123; Xia, et al.; Notice of Allowance dated May 4, 2016; filed May 14, 2013.
U.S. Appl. No. 13/894,123; Xia, et al.; Statement of the Substance of Interview filed May 12, 2016; filed May 14, 2013.
U.S. Appl. No. 13/894,123; Xia, et al.; Notice to File Corrected Application Papers dated Aug. 15, 2016; filed May 14, 2013.
U.S. Appl. No. 13/894,123; Xia, et al.; Response to Notice to File Corrected Application Papers filed Oct. 12, 2016; filed May 14, 2013.
U.S. Appl. No. 15/221,196; Xia et al.; Office Action dated Oct. 18, 2016; filed Jul. 27, 2016.
U.S. Appl. No. 15/221,196; Xia et al.; Response to Office Action filed Dec. 7, 2016; filed Jul. 27, 2016.
U.S. Appl. No. 15/221,196; Xia et al.; Office Action dated Feb. 3, 2017; filed Jul. 27, 2016.
U.S. Appl. No. 15/221,196; Xia et al.; Response to Office Action filed Jun. 15, 2017; filed Jul. 27, 2016.
U.S. Appl. No. 15/221,196; Xia et al.; Notice of Allowance dated Aug. 25, 2017; filed Jul. 27, 2016.
U.S. Appl. No. 15/221,196; Xia et al.; Notice of Allowance dated Sep. 20, 2017; filed Jul. 27, 2016.
U.S. Appl. No. 15/221,196; Xia et al.; Amendment Under 37 CFR 1.312 filed Oct. 5, 2017; filed Jul. 27, 2016.
U.S. Appl. No. 15/221,196; Xia et al.; Response to Rule 312 Communication dated Oct. 13, 2017; filed Jul. 27, 2016.
U.S. Appl. No. 15/221,196; Xia et al.; Notice of Abandonment dated Dec. 13, 2017; filed Jul. 27, 2016.
U.S. Appl. No. 15/822,666; Xia, et al.; Preliminary Amendment filed Jun. 13, 2018; filed Nov. 27, 2017.
U.S. Appl. No. 15/322,565; Wolpe, Stephen D.; Office Action dated Jul. 5, 2017; filed Dec. 28, 2016.
U.S. Appl. No. 15/322,565; Wolpe, Stephen D.; Response to Office Action filed Aug. 22, 2017; filed Dec. 28, 2016.
U.S. Appl. No. 15/322,565; Wolpe, Stephen D.; Office Action dated Sep. 8, 2017; filed Dec. 28, 2016.
U.S. Appl. No. 15/322,565; Wolpe, Stephen D.; Amendment and Response to Office Action filed Mar. 8, 2018; filed Dec. 28, 2016.

(56) References Cited

OTHER PUBLICATIONS

U.S. Appl. No. 15/322,565; Wolpe, Stephen D.; Final Office Action dated Apr. 3, 2018; filed Dec. 28, 2016.
U.S. Appl. No. 12/997,230; Miller, et al.; Office Action dated Nov. 26, 2012; filed Dec. 9, 2010.
U.S. Appl. No. 12/997,230; Miller, et al.; Amendment and Response to Office Action filed Mar. 26, 2013; filed Dec. 9, 2010.
U.S. Appl. No. 12/997,230; Miller, et al.; Office Action dated Aug. 15, 2013; filed Dec. 9, 2010.
U.S. Appl. No. 12/997,230; Miller, et al.; Notice of Abandonment dated Mar. 18, 2014; filed Dec. 9, 2010.
U.S. Appl. No. 14/182,141; Wolpe, et al.; Office Action dated Jan. 2, 2015; filed Feb. 17, 2014.
U.S. Appl. No. 14/182,141; Wolpe, et al.; Response to Office Action filed Jun. 30, 2015; filed Feb. 17, 2014.
U.S. Appl. No. 14/182,141; Wolpe, et al.; Office Action dated Jul. 20, 2015; filed Feb. 17, 2014.
U.S. Appl. No. 14/182,141; Wolpe, et al.; Response to Office Action filed Jan. 20, 2016; filed Feb. 17, 2014.
U.S. Appl. No. 14/182,141; Wolpe, et al.; Office Action dated May 9, 2016; filed Feb. 17, 2014.
U.S. Appl. No. 14/182,141; Wolpe, et al.; Notice of Abandonment dated Dec. 1, 2016; filed Feb. 17, 2014.
U.S. Appl. No. 10/854,723; Christopherson II, et al; Office Action dated Sep. 21, 2006; filed May 26, 2004.
U.S. Appl. No. 10/854,723; Christopherson II, et al; Response to Office Action filed Jan. 22, 2007; filed May 26, 2004.
U.S. Appl. No. 10/854,723; Christopherson II, et al; Final Office Action dated Apr. 13, 2007; filed May 26, 2004.
U.S. Appl. No. 10/854,723; Christopherson II, et al; Response to Final Office Action dated Aug. 13, 2007; filed May 26, 2004.
U.S. Appl. No. 10/854,723; Christopherson II, et al; Advisory Action dated Sep. 4, 2007; filed May 26, 2004.
U.S. Appl. No. 10/854,723; Christopherson II, et al; Notice of Abandonment dated Oct. 26, 2007; filed May 26, 2004.
U.S. Appl. No. 11/872,641; Christopherson II, et al; Office Action dated Oct. 1, 2009; filed Oct. 15, 2007.
U.S. Appl. No. 11/872,641; Christopherson II, et al; Response to Office Action filed Mar. 31, 2010; filed Oct. 15, 2007.
U.S. Appl. No. 11/872,641; Christopherson II, et al; Final Office Action dated Jun. 24, 2010; filed Oct. 15, 2007.
U.S. Appl. No. 11/872,641; Christopherson II, et al; Notice of Abandonment dated Jan. 3, 2011.
U.S. Appl. No. 12/971,496; Christopherson II, et al; Office Action dated Feb. 16, 2011;filed Dec. 17, 2010.
U.S. Appl. No. 12/971,496; Christopherson II, et al; Notice of Abandonment dated Aug. 31, 2011.
Capela, et al.; "LeX/ssea-1 Is Expressed by Adult Mouse CNS Stem Cells, Identifying Them as Nonependymal," Neuron, (Aug. 2002), vol. 35, pp. 865-875.
Frenette, et al.; "Endothelial Selectins and Vascular Cell Adhesion Molecule-1 Promote Hematopoietic Progenitor Homing to Bone Marrow," Proce. Natl. Acad. Sci. USA, (Nov. 1998), vol. 95, pp. 14423-14428.
Grabel, et al.; "Teratocarcinoma Stem Cell Adhesion: The Role of Divalent Cations and a Cell Surface Lectin," The Journal of Cell Biology, (Jun. 1983), vol. 96, pp. 1532-1537.
Katayama, et al.; "PSGL-1 Participates in E-selectin-mediated Progenitor Homing to Bone Marrow: Evidence for Cooperation Between E-Selectin Ligands and α4 Integrin," Blood, (Sep. 15, 2003), vol. 102, No. 6, pp. 2060-2067.
Sackstein, et al.; "Ex Vivo Glycan Engineering of CD44 Programs Human Multipotent Mesenchymal Stromal Cell Trafficking to Bone," Nature Medicine, (Feb. 2008), vol. 14, No. 2, pp. 181-187.
Xia, et al.; "Surface Fucosylation of Human Cord Blood Cells Augments Binding to P-Selectin and E-Selectin and Enhances Engraftment in Bone Marrow," Blood, (Jul. 27, 2004), vol. 104, pp. 3091-3096.
Homeister, et al.; "The α(1,3)Fucosyltransferases FucT-IV and FucT-VII Exert Collaboratibe Control over Selectin-Dependent Leukocyte Recruitment and Lymphocyte Homing," Immunity Jul. 2001), vol. 15, pp. 115-126.
Sultana, et al.; "Expression of Functional P-Selectin Glycoprotein Ligand 1on Hematopoietic Progenitors Is Developmentally Regulated," The Journal of Immunology (Mar. 2012), vol. 188, pp. 4385-4393.
Kawashima, Hiroto; "Roles of Sulfated Glycans in Lymphocyte Homing," Biol. Pharm. Bull. (2006), vol. 29, No. 12, pp. 2343-2349.
Parmar, et al.; "Ex Vivo Fucosylation of Third-party Human Regulatory T Cells Enhances Anti-Graft-Versus-Host Disease Potentcy in Vivo," Blood (2015), vol. 125, No. 9, pp. 1502-1506.
Chen, et al.; "T Regulatory Cells and Migration," American Journal of Transplantation (2006), vol. 6, pp. 1518-1523.
Kobzdej, et al.; "Discordant Expression of Selectin Ligands and Sialyl Lewis X-related Epitopes on Murine Mycloid Cells," Blood, (Dec. 2002), vol. 100, No. 13, pp. 4485-4494.

\* cited by examiner

A

B

AUGMENTATION OF CELL THERAPY EFFICACY INCLUDING TREATMENT WITH ALPHA 1,3 FUCOSYLTRANSFERASE

CROSS-REFERENCE TO RELATED APPLICATIONS/INCORPORATION BY REFERENCE STATEMENT

This application is a continuation of U.S. Ser. No. 15/347,500, filed Nov. 9, 2016, now abandoned; which is a continuation of U.S. Ser. No. 14/182,141, filed Feb. 17, 2014, now abandoned; which is a continuation-in-part of U.S. Ser. No. 12/997,230, filed Jun. 9, 2009, now abandoned; which is a US national stage application filed under 35 USC § 371 of International Application No. PCT/US2009/046800, filed Jun. 9, 2009; which claims priority to U.S. Provisional Application No. 61/060,084, filed Jun. 9, 2008. The entire contents of each of the above-referenced patents and patent applications are hereby expressly incorporated by reference.

BACKGROUND

Cell therapy offers immense possibilities for treatment of a wide variety of medical conditions. Currently cell therapy is practiced in numerous embodiments, for example, bone marrow transplantation for treatment of hematopoietic malignancies. The successful establishment of procedures for transplantation of donor cells into recipients whose own cells are malignant (leukemia), altered (stroke, limb ischemia, etc.), or insufficient (due to chemotherapy, radiotherapy, or congenital abnormality) constitutes a major medical breakthrough in the therapeutic management of these conditions.

One limiting factor of any cell therapy is the need for blood-borne or directly injected cells to migrate to the targeted tissue in order to maximize their therapeutic potential. With regard to hematopoietic stem cells as a particular example, it is known that only a small percentage of these cells home to the bone marrow microenvironment when administered systemically. This migration is regulated in part by adhesive factors present on the luminal surface of endothelial cells that constitute the microvascular lining of the bone marrow and in part by chemotactic gradients secreted at a constant rate by bone marrow stromal cells. In addition, for the treatment of myocardial infarction or stroke, only a small fraction of injected stem cells actually home and enter the area of tissue damage. Thus, there exists a need to administer a high number of stem cells, sometimes prohibitively too high to be obtained in an autologous or even allogeneic setting.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
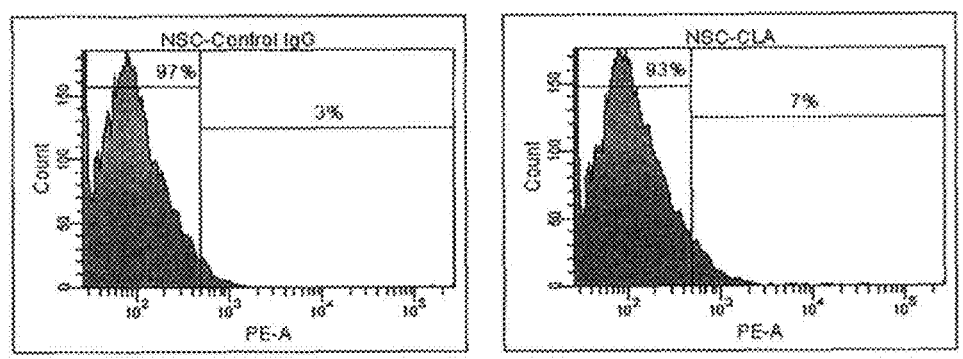
FIG. 1 illustrates the effect of pretreatment of human neural stem cells (HNSCs) with α1,3 fucosyltransferase-VI (FTVI) on the level of fucosylation. The expression of CLA was used to determine the levels of fucosylation. The CLA expression by hNSCs was determined by FACS analysis with untreated cells (A) or following pre-incubation with the fucosylation mix (GDP-Fucose, manganese and FTVI conditioned medium) (B). Isotype-matched IgG was used as the negative control. Fluorescence intensity (FL2) of samples was evaluated by FACSCanto™ cell analyzer (BD Biosciences, San Jose, CA). The results of one experiment are shown.
Figure 1:
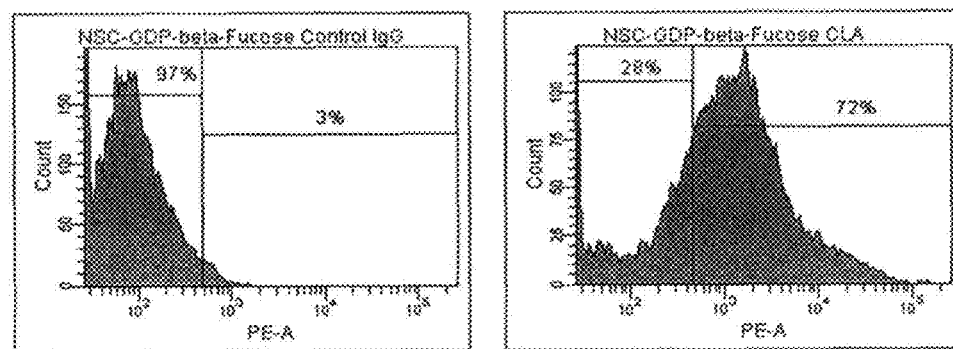

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation, and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The ability of cells such as leukocytes to interact with the endothelium has been known for decades. It has also been known that various glycosylation patterns are critical for cells such as leukocytes to "roll" on the endothelium prior to extravasation. What is desirable is the identification of novel methods that enhance cell trafficking and engraftment to areas of need in a simple and clinically applicable manner.

The present embodiments relate generally to the field of cell therapy. More specifically, some embodiments relate to methods of enhancing the natural process of cell migration through augmentation of specific glycosylation features on the surface of various cell types. More specifically, some embodiments relate to treatment of cells with fucosyltransferases in order to enhance the interaction between blood-borne stem cells, progenitor cells and endothelial cells facilitating entry into biological niches and tissues where they may function on a number of different levels for therapeutic and restorative intervention.

Accordingly, provided herein in certain embodiments are methods of enhancing homing and engraftment of therapeutically-administered cells in a patient. It should be noted that the term "patient" is meant to broadly include any animal. For example, the animal can be a mammal, a bird, a fish, a reptile, a fish, an insect or any other animal. Some non-limiting examples of mammals may include humans and other primates, equines such as horses, bovines such as cows, mice, rats, rabbits, Guinea Pigs, pigs, and the like. It is also worth noting that the compositions and methods can be used with or applied to individual cells (for example ex vivo treatment or modification), to insect cells, etc. Also provided are cells that have been modified to enhance homing and engraftment. The embodiments provided herein are based in part on the surprising finding that by modification of molecules involved in the cell-endothelium interaction, it is possible to enhance the homing and subsequent efficacy of cell therapy.

One embodiment provides a method of enhancing homing and engraftment of a therapeutically-administered cell in a patient in need of treatment with a cell population; providing cells that may have been contacted with an agent that modifies at least one surface molecule on the cells, resulting in a population of modified cells; and providing or administering the population of modified cells to a patient in need thereof. In certain aspects, the cell surface molecule may be modified so as to result in an alteration of cell charge.

In one embodiment, a method of enhancing homing and engraftment of a cell may comprise providing one or more cells selected from stem cells, progenitor cells, neutrophils, macrophages, T-cells, and combinations thereof. The stem or progenitor cells may be embryonic stem cells, adult stem cells, expanded stem cells, placental stem cells, bone marrow stem cells, amniotic fluid stem cells, neuronal stem cells, cardiomyocyte stem cells, placental stem cells, endothelial progenitor cells, circulating and mobilized peripheral blood stem cells, muscle stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells, or somatic nuclear transfer and side population stem cells, as well as any combination thereof. One or more cells may have been contacted with an agent that modifies at least one surface molecule on the cell that may result in enhanced selectin-mediated binding. This may result in a population of modified cells. These cells may be provided to animals. Such animals may include birds, reptiles, fish, insects, and mammals including but not limited to humans, equines such as horses, bovines such as cows, dogs, mice, rats, pigs, guinea pigs, rabbits and the like.

In certain aspects of the above embodiments, the cell surface molecule may be modified by treatment with an enzyme and appropriate substrate(s) under conditions sufficient for causing an alteration of cell surface charge. In certain aspects, the enzyme may be a glycosidase, glycosyltransferase, a fucosyltransferase, a neuraminidase, an acetylglucosaminyltransferase, or any glycosyltransferase capable of increasing the number or affinity of cell surface selectin binding components. In certain aspects, the enzyme may be alpha 1,3-fucosyltransferase I, alpha 1,3-fucosyltransferase III, alpha 1,3-fucosyltransferase IV, alpha 1,3-fucosyltransferase V, alpha 1,3-fucosyltransferase VI, alpha 1,3-fucosyltransferase VII, or alpha 1,3-fucosyltransferase IX.

In another aspect of the above embodiment, the cell may be treated with a reagent or reagents that link a binding unit to the cell surface. The binding unit may consist of a particle as well as a ligand of natural or non-natural sugars shown to possess binding affinity for receptors present on endothelial cells similar to that seen with natural sugars. The added binding unit may increase the functionalization of the cell.

In certain further aspects of the above embodiment, the cell may be treated with a single or plurality of molecules having ability to cause alpha 1-3 fucosylation of glycan determinants. In certain aspects, the molecule may be an alpha 1-3 fucosyltransferase mixed together with a concentration of a fucose carrier under conditions sufficient to provide enhanced alpha 1-3 fucosylation of glycan determinants. In certain aspects, the fucose carrier may be guanosine diphosphate fucose. In certain aspects, the alpha 1-3 fucosyltransferase may be alpha 1-3 fucosyltransferase VI. In other aspects, the alpha 1-3 fucosyltransferase may be alpha 1-3 fucosyltransferase VII. In other aspects, the alpha 1-3 fucosyltransferase may be alpha 1-3 fucosyltransferase IV.

In certain aspects of the above embodiment, prior to the providing or administering, the population of modified cells has been further contacted for a period of time insufficient for cell division to occur with a CD26 peptidase inhibitor in an amount effective to inhibit CD26 peptidase activity and effective to increase the migratory response to CXCL12. PCT Publication WO 2009/152186, which is incorporated herein by reference in its entirety, discloses and describes methods and compositions, any of which can be used with the technology of this application in any combination.

In certain aspects, prior to providing modified cells, a recipient may be contacted for a period of time and with sufficient dosing of a CD26 peptidase inhibitor in an amount effective to inhibit recipient CD26 peptidase activity effective to increase the migratory response of donor cells to chemotractant agents such as stromal cell-derived factor.

In certain aspects, the cell population may comprise or consist essentially of a population of stem cells, both embryonic and adult and expanded cell populations. In certain aspects, the stem cells may be embryonic stem cells, cord blood stem cells, placental stem cells, bone marrow stem cells, amniotic fluid stem cells, hematopoietic stem cells, mesenchymal stem cells, neuronal stem cells, cardiomyocyte stem cells, circulating and immobilized peripheral blood stem cells, endothelial progenitor cells, monocyte-derived stem cells, muscle stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells or somatic nuclear transfer and side population stem cells. In certain aspects, the embryonic stem cells may be totipotent. In certain aspects, the stem cell may be hematopoietic, mesenchymal, neural or cardiomyocyte stem cells. In certain aspects the hematopoietic stem cells may be further defined and differentiated as CD38-, lin- or ALDH-bright cells.

In certain aspects, the cell population may comprise or consist essentially of a population of committed progenitor cells or differentiated cells. In certain aspects, the cell population may be a mature blood cell population. In certain aspects, the mature blood cell may be neutrophils, macrophages, T-cells, activated T-cells, helper T cells, cytolytic T-cells, memory T-cells, regulatory T-cells, natural killer (NK) cells, or reprogrammed cells. In certain aspects, the T-cells may be from a heterogeneous population of T-cells.

In certain aspects, the patient in need of treatment with a cell population suffers from a malignant or non-malignant blood disorder such as an acute leukemia, a chronic leukemia, a myelodysplastic syndrome, a stem cell disorder, a myeloproliferative disorder, a lymphoproliferative disorder, a phagocyte disorder, a histiocytic disorder, a lysosomal storage disease, an age related disorder, an arterial or blood vessel or cardiovascular disorder, an enzyme deficiency disorder, a congenital immune system disorder, an inherited erythrocyte abnormality, an inherited platelet abnormality, a plasma cell disorder, a tumor or an autoimmune disease. In certain aspects, the patient in need of treatment with a cell population may suffer from peripheral arterial diseases, ischemic limb injury, diabetes, heart disease, bone disease, liver disease, muscular dystrophy, Alzheimer's disease, ALS, multiple sclerosis, Parkinson's disease, spinal cord injury, stroke or infertility.

In certain aspects, the population of modified cells may be administered intravenously, intraarterially, intramuscularly, subcutaneously, transdermally, intratracheally, intraperitoneally, intrathecally intracranially, intravitreally, or directly into the microvascular compartment of bone or into spinal fluid. In certain aspects, the population of modified cells may be administered in or proximal to a site of injury. In certain aspects, the homing and engraftment may take place within the bone marrow of the patient in need thereof.

In another embodiment, a composition may comprise an isolated population of cells modified for enhanced selectin-mediated binding. The isolated population of cells may be neutrophils, macrophages, T-cells, subpopulation of T-cells, or stem or progenitor cells selected from a group consisting of: embryonic stem cells, adult stem cells, expanded stem cells, placental stem cells, bone marrow stem cells, amniotic fluid stem cells, neuronal stem cells, cardiomyocyte stem cells, endothelial progenitor cells, circulating and mobilized peripheral blood stem cells, muscle stem cells, germinal stem cells, adipose tissue derived stem cells, exfoliated teeth derived stem cells, hair follicle stem cells, dermal stem cells, parthenogenically derived stem cells, or reprogrammed stem cells such as induced pluripotent stem cells or somatic nuclear transfer and side population stem cells and a pharmaceutically-acceptable carrier.

In certain aspects, the isolated population may comprise a cell surface modification. In certain aspects, the cell surface molecule may be modified by treatment with an enzyme and appropriate substrate(s) under conditions sufficient for causing an alteration of cell surface charge.

In certain aspects, the enzyme is selected from a group comprising of: a glycosidase, a glycosyltransferase, a fucosyltransferase, a neuraminidase, and an acetylglucosaminyl-transferase or any other glycotransferases capable of increasing cell surface selectin binding components. In certain aspects, the enzyme is selected from a group comprising of alpha 1,3-fucosyltransferase I, alpha 1,3-fucosyltransferase III, alpha 1,3-fucosyltransferase IV, alpha 1,3-fucosyltransferase V, alpha 1,3-fucosyltransferase VI, alpha 1,3-fucosyltransferase VII and alpha 1,3-fucosyltransferase IX.

In certain aspects, the cell may be treated with a single or plurality of molecules having ability to cause alpha 1-3 fucosylation of glycan determinants. In certain aspects, the molecule may be an alpha 1-3 fucosyltransferase mixed together with a concentration of a fucose carrier under conditions sufficient to provide enhanced alpha 1-3 fucosylation of glycan determinants. In certain aspects, the fucose carrier may be guanosine diphosphate fucose. In certain aspects, the alpha 1-3 fucosyltransferase may be alpha 1-3 fucosyltransferase VI. In certain aspects, the alpha 1-3 fucosyltransferase may be alpha 1-3 fucosyltransferase VII. In certain aspects the alpha 1-3 fucosyltransferase may be alpha 1-3 fucosyltransferase IV. In certain aspects the molecule may be a non-naturally occurring enzyme having the ability to add a glycan determinant or a non-natural sugar that mimics the activity of fucose or other sugars that enhance the selectin binding process.

In certain aspects, the cell population may comprise or consist essentially of a population of stem cells both embryonic and adult. In certain aspects, the stem cells may be embryonic stem cells, cord blood stem cells, placental stem cells, bone marrow stem cells, amniotic fluid stem cells, hematopoietic stem cells, mesenchymal stem cells, neuronal stem cells, cardiomyocyte stem cells, circulating and mobilized peripheral blood stem cells, endothelial progenitor cells, monocyte-derived stem cells, muscle stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells or somatic nuclear transfer and side population stem cells. In certain aspects, the embryonic stem cells may be totipotent. In certain aspects, the stem cell may be hematopoietic, mesenchymal, neural or cardiomyocyte stem cells.

In certain aspects, the cell may be a mature blood cell. In certain aspects, the mature blood cell may be a neutrophil, macrophage, or T-cell. In certain aspects, the T-cells may be from a heterogeneous population of T-cells or from an ex vivo expanded cell population.

Another embodiment provides a method of enhancing homing and engraftment of a cell, comprising providing one or more cells selected from stem cells, progenitor cells, neutrophils, macrophages and T-cells. The stem or progenitor cells may be embryonic stem cells, adult stem cells, expanded stem cells, placental stem cells, bone marrow stem cells, amniotic fluid stem cells, neuronal stem cells, cardiomyocyte stem cells, endothelial progenitor cells, circulating and immobilized peripheral blood stem cells, muscle stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells or somatic nuclear transfer and side population stem cells. One or more cells may be contacted with an agent that modifies at least one surface molecule on the cell(s) to result in enhanced selectin-mediated binding, resulting in a population of modified cells.

Also provided herein is a method of fucosylation of cells so as to increase the ability of the cells to traffic, home and engraft into an area of biological need. The cells may be mature fully differentiated cells whose homing to specific targets is desired, such as islets, hepatocytes, or neutrophils or cells may be progenitor cells capable of differentiating into functional cells such as hepatic, renal, cardiac, or islet progenitors, or alternatively, the cells may be stem cells with multilineage differentiation ability such as embryonic stem cells, cord blood stem cells, placental stem cells, bone marrow stem cells, amniotic fluid stem cells, neuronal stem cells, circulating and mobilized peripheral blood stem cells, mesenchymal stem cells, endothelial stem cells, cardiomyocyte stem cells, germinal stem cells, committed endothelial progenitor cells, committed progenitor cells, adipose tissue derived stem cells, exfoliated teeth derived stem cells, hair follicle stem cells, dermal stem cells, parthenogenically derived stem cells, chemically, biologically, or electronically reprogrammed stem cells such as induced pluripotent stem cells or somatic nuclear transfer and side population of stem cells.

Other aspects relate to enhancing the ability of cells to modulate the immune system through enabling the cells to function with augmented efficiency at trafficking and homing. In another aspect, cells useful for immune therapy are "reprogrammed" ex vivo with endowment of distinct immunological properties. Surface modification may be performed before reprogramming, during reprogramming or after reprogramming. Reprogramming may be performed so as to increase immune stimulatory properties of the immune cells, or may be performed to allow the immune cells to suppress other immune cells. Reprogramming may be performed during expansion of cells, or to cells that have already been expanded.

In certain aspects, the cells can be fucosylated so as to enhance ability to home. Fucosylation may be performed on specific molecules present on the cells, or may be performed globally in a non-specific manner. Cells may be fucosylated through culture with an enzyme such as a fucosyltransferase capable of transferring fucose groups such as a fucosyltransferase. In certain aspects, the fucosyltransferase may be an alpha 1,3 fucosyltransferase. In another aspect the enzyme is selected from a group comprising of alpha 1,3-fucosyltransferase IX, alpha 1,3-fucosyltransferase III, alpha 1,3-fucosyltransferase IV, alpha 1,3-fucosyltransferase V, alpha 1,3-fucosyltransferase VI and alpha 1,3-fucosyltransferase VII. Appropriate culture conditions and substrates are also provided within the scope of the embodiments in order to allow proper fucosylation to occur. The conditions may include addition of substrates such as GDP-fucose or other similar compounds that provide a source of fucose.

In certain aspects, cells may be treated with a single or plurality of agents in order to augment expression of proteins involved in migration. Since the proteins involved in migration, when expressed de-novo, are not properly fucosylated, the addition of exogenous fucose groups increases ability of the de-novo expressed proteins to interact with endothelium and properly home. Specific molecules may include histone deacetylase inhibitors or DNA methyltransferase inhibitors.

Some embodiments relate generally to compositions for and methods of enhancing homing and engraftment of a therapeutically-administered cell in a patient. Also, some embodiments relate to cells that have been modified to enhance homing and engraftment. The embodiments provided herein are based in part on the surprising finding that by modification of molecules involved in the cell-endothelium interaction, it is possible to enhance the homing and subsequent efficacy of cell therapy.

The process by which cells exit the systemic circulation and enter distinct biologically niches is a complex coordinated process that involves numerous molecules. The process of cellular exit is a bi-directional communication between the vascular endothelium cells and the circulating stem and progenitor cells. This process has been best characterized in the description of leukocyte exit from systemic circulation. An important family of molecules involved critically and initially in the process of cellular trafficking is the selectins. These molecules are type 1 transmembrane proteins that contain what is known as C-type lectin domains. Lectins are proteins that bind sugars. Most commonly known lectins include conconavalin-A and phytohemagglutinin. The C-type lectin domains on the selectins reside at the N-terminal of the selectins and interact with a wide array of glycoprotein ligands. Since the lectin domains bind sugar moieties, it is important that proper placement of sugars onto the proteins such that interaction of the selectins occurs. Since placement of sugars (glycosylation) usually occurs as a post-translational event, the mere genetic manipulation of cells is not sufficient usually to alter ability of cells to interact with selectins. The exception to this is, of course, genetic manipulation in the sense of transfecting cells with enzymes that are involved in the addition of sugars.

Provided herein are means of endowing enhanced trafficking/homing capabilities onto cells for use in cell therapy, said means consisting of modification of various glycosylation patterns on cells in order to augment ability to "roll", "tether", and "adhere" on the endothelium. The concept of cells rolling, tethering, and adhering on the endothelium is commonly known in the art and means of augmentation of this rolling process have been described strictly in the areas of hematopoietic cells, as well as tumor cells.

Previous studies with hematopoietic cells have demonstrated that it is possible to alter glycosylation and fucosylation patterns on the surface of cells by treating of cells with enzymes such as fucosyltransferases. In addition to establishing the ability to modify the surface of cells, the functional consequences of this modification have been documented. Specifically, several reports (Xia et al., Blood 2004 104:3091-3096; Hidalgo, et al., J. Clin. Invest. 2002 110: 559-569, each of which is hereby incorporated by reference in its entirety) demonstrated that fucosylation of cord blood hematopoietic cells enhances binding of P and E selectin, enhances ex vivo binding to P and E-selectin-coated plates under physiological shear stress conditions and enhances homing and engraftment into bone marrow of NOD-SCID mice. (See also U.S. Pat. No. 7,332,334 and US Pub. No. 2006/0228340 to Xia and McEver, each of which is hereby incorporated by reference in its entirety). Findings in mesenchymal stem cells have also been described by others, including Sackstein et al. (US 2003/0040607 and US 2008/0044383, each of which is incorporated by reference in its entirety). Each reference listed in this paragraph is incorporated herein by reference in its entirety.

However another report demonstrated that while early (minutes to hours following iv injection) adhesion of cord blood hematopoietic cells is increased after ex vivo fucosylation, no increase in bone marrow homing at 16-24 hrs was observed (Hidalgo and Frenette, Blood 2005 105:567-575, which is incorporated herein by reference in its entirety).

It has been suggested by Sackstein et al. that mesenchymal stem cells, which do not express E-selectin ligands, can be glycosylated enzymatically in an effort to enhance migration of these cells to the bone marrow (Sackstein et al. Nature Medicine 2008 14:181-187; which is incorporated herein by reference in its entirety).

Thus, embodiments presented herein are based in part on the novel observation that fucosylation of ligands increases binding to tissue and can be used to enhance migration of various types of cells, enumerated herein, to an area of need. Specifically, some embodiments provided herein relate in part to the surprising finding that augmentation of the tethering and rolling process through various means is useful for enhancing functional capabilities of a wide variety of non-hematopoietic cells and stem cells. Accordingly, the methods and compositions provided herein may be useful for treatment of a wide variety of medical conditions that are amenable to cell therapy.

Therapeutic Methods

In accordance with the above, provided herein are methods of enhancing homing and engraftment of a therapeutically-administered cell in a patient. Specifically, provided herein are methods of modification of sugar residues, both natural and non-natural, on the surface of cells used for cell therapy so as to enhance their interaction with members of the selectin family, thereby enhancing trafficking of the cells administered systemically to an area of need.

Also provided are cells that have been modified to enhance homing and engraftment. The embodiments provided herein are based in part on the surprising finding that by modification of molecules involved in the cell-endothelium interaction, it is possible to enhance the homing and subsequent efficacy of cell therapy.

Examples of cells include, without being limited thereto, neutrophils, macrophages and T-cells, wherein the stem or progenitor cells are selected from a group consisting of: embryonic stem cells, adult stem cells, expanded stem cells, placental stem cells, bone marrow stem cells, hematopoietic stem cells, mesenchymal stem cells, amniotic fluid stem cells, neuronal stem cells, cardiomyocyte stem cells, endothelial progenitor cells, circulating and mobilized peripheral blood stem cells, muscle stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells or somatic nuclear transfer and side population stem cells. In some aspects, one or more of the cell types mentioned can be specifically excluded from the methods or compositions described herein. As one example, in some aspects mesenchymal or hematopoietic stem cells can be excluded.

In one embodiment is provided a method of enhancing homing and engraftment of a therapeutically-administered cell in a patient comprising selecting a patient in need of treatment with a cell population; providing cells that have been contacted with an agent that modifies at least one surface molecule on the cells, resulting in a population of modified cells; and providing or administering the population of modified cells to a patient in need thereof. In certain aspects, the cell surface molecule is modified so as to result in an alteration of cell charge.

Modification Enzymes

In certain aspects of the above embodiments, the cell surface molecule is modified by treatment with an enzyme and appropriate substrate(s) under conditions sufficient for causing an alteration of cell surface charge. Enyzmes that modify cell surface molecules are known in the art. Such enzymes include a purified glycosyltransferase polypeptide. Glycosyltransferase include for example, fucosyltransferase, galactosyltransferase, sialytransferase and N-acetylglucosaminotransferase. The fucosyltransferase can be, for example, an alpha 1,3 fucosyltransferase such as an alpha 1,3-fucosyltransferase I, alpha 1,3-fucosyltransferase III, alpha 1,3-fucosyltransferase IV, alpha 1,3-fucosyltransferase V, alpha 1,3-fucosyltransferase VI, alpha 1,3-fucosyltransferase VII, and alpha 1,3-fucosyltransferase IX. It should be noted that in some embodiments, one or more of the enzymes listed herein can be specifically excluded. For example, in some aspects, FTVI can be specifically excluded from the methods and compositions described herein.

In certain aspects, the cell surface molecule is modified in the presence of a sugar donor suitable for the specific glycosyltransferase. Sugar donors for glycosyltransferases are known in the art. For example, when the glycoslytransferase is a fucosyltransferase, the donor is GDP-fucose. Whereas, when the glycosyltransferase is a siayltransferase, the donor is eMP-sialic acid. In some instances the sugar can be a non-natural sugar added by a natural or modified glycosyltransferase.

The glycosyltransferases are biologically active. By biologically active is meant that the glycosyltransferases are capable of transferring a sugar molecule from a donor to acceptor. For example, the glycosyltransferase is capable of transferring 0.1, 0.2, 0.3, 0.4, 0.5, 1.0, 1.5, 2.0, 2.5, 5, 10 or more μmoles of sugar per minute at pH 6.5 at 37° C.

Physiologically acceptable solution is any solution that does not cause cell damage, e.g. death. For example, the viability of the cell or cell particle is at least 80%, 85%, 90%, 95%, 96%, 97%, 98%, 99% or more after treatment according to the methods presented herein. Suitable physiologically acceptable solutions include for example, Hank's Balanced Salt Solution (HBSS), Dulbecco's Modified Eagle Medium (DMEM), a Good's buffer (see N. E. Good, G. D. Winget, W. Winter, T. N. Conolly, S. Izawa and R. M. M. Singh, Biochemistry 5, 467 (1966); N. E. Good, S. Izawa Methods Enzyrnol. 24, 62 (1972) such as a HEPES buffer, a 2-Morpholinoethanesulfonic acid (MES) buffer, or phosphate buffered saline (PBS). Each reference listed in this paragraph is incorporated herein by reference in its entirety.

Thus, in certain embodiments provided herein, cells can be treated ex vivo with a kit that contains some or all of the agents, such as enzyme, buffer, cofactors and substrate necessary to achieve fucosylation of the cell surface glycoproteins that mediate adhesive interactions between the circulating cells following iv administration and endothelial cells at targeted tissue sites. In another embodiment provided herein, cells such as cord blood can be pretreated with the fucosylation kit prior to freezing or storage.

In certain aspects, the syn-anti and/or α-β substitution and orientation of the polysaccharide are modulated to provide the desired effect. Cell surface oligosaccharides are highly diversified in their structures and are associated with a variety of cell functions. In an inflammatory response, for example, neutrophils or leukocytes bind to injured tissues where the adhesion process occurs. This process has been found to be mediated by the tetrasaccharide sialyl Lewis X on neutrophiles or leukocytes and the receptor ELAM-1 (endothelial leukocyte adhesion molecule 1), a glycoprotein of the selectin family. Several sialyl lewis analogues and mimetics have been analyzed, in part, to understand affects of syn versus anti sugar conformers. Similar studies have examined fucosyl and galactosyl conformers, diastereomers, epimers and chiral analogues to examine adhesion and inhibitory properties. See Ichikawa Y et al. *J. Am. Chem. Soc.* 1992, 114, 9283-9298; Nelson, Richard M. et al *J. Clin. Invest.* 1993, 1157-1166; Chun-Cheng Lin et al, *J. Am. Chem. Soc.* 1996, 118, 6826-6840; Clarke Julia L. *J Am. Chem. Soc.* 1996, 118, 6826-6840; Chikara Ohyama, et al, The EMBO Journal Vol. 18 No. 6 pp. 1516-1525, 1999; each of which is incorporated herein by reference in its entirety. Each reference listed in this paragraph is incorporated herein by reference in its entirety.

The introduction of fucose onto surface glycans of the cells of interest can be accomplished by enzymatic transfer from a donor substrate utilizing an alpha 1-3-fucosyltransferase (FT) by a process well known to someone skilled in the art. For this transfer to occur the cells at varying concentrations can be exposed to an incubation buffer containing a number of ingredients each of which can be optimized for efficient transfer of the fucose. The selection of buffer can come from a number of available buffers with Hanks balanced salt solution (HBSS) serving as the primary example. The substrate, guanosine diphosphate-fucose (GDP-fucose), at 1 mM can be mixed with the FT added at sufficient activity, expressed as Units/mL, to achieve maximal transfer of fucose to the cells of interest. In addition, MnC12 at a final concentration of 0-10 mM can be added, if needed, depending on the cell population to further accelerate the enzymatic transfer reaction. The temperature and time of incubation can also be optimized for maximal transfer of fucose under practical application conditions with minimum toxicity to the cells of interest but is generally conducted at 37° C. for 40 minutes.

Confirmation of fucosylated epitopes on the cells of interest as means of confirming maximal levels of fucosylation can be verified by Flow Cytometry utilizing agents and procedures well known to someone skilled in the art. For example, sialyl LewisX is a fucosylation epitope found on both P and E-selectins. By incubation of the FT-treated cells with anti-sLeX mAb HECA 452 (IgM) followed by treatment with FITC-conjugated fragment to the IgM, the sLeX epitopes on the cell surface can be visualized using standard Flow Cytometry procedures.

Combination Treatment with CD26 Peptidase Inhibitors

In certain aspects of the above embodiment, prior to the administering, the population of modified cells has been further contacted for a period of time insufficient for cell division to occur with a CD26 peptidase inhibitor in an amount effective to inhibit CD26 peptidase activity and effective to increase the migratory response to CXCL12.

Exemplary methods of treating stem cells with CD26 (dipeptidylpeptidase) inhibitors are described in Christopherson et al. (US Pub No. 2004/0247574, incorporated by reference in its entirety). In certain aspects, the CD26 inhibitor is selected from the group consisting of Diprotin A (Ile-Pro-Ile), Valine-Pyrrolidide, sitagliptin, vildagliptin, saxagliptin, alogliptin or any other class of compounds shown to exhibit potent inhibition of either purified, soluble or cell surface (CD26) dipeptidylpeptiase. PCT Publication WO 2009/152186, which is incorporated herein by reference in its entirety, discloses and describes methods and compositions, any of which can be used with the technology of this application in any combination.

In certain aspects, the cell population is contacted with said CD26 inhibitor for about 5 minutes to about 12 hours or conditions suitable for sufficient inhibition of cell surface CD26 leading to an enhanced migratory response to chemotactic factors such as stromal cell-derived factor. In certain aspects, the cell population is contacted with said CD26 inhibitor for about 5 minutes to about 12 hours. In certain aspects, the cell population is contacted with said CD26 inhibitor for less than 6 hours. In certain aspects, the cell population is contacted with said CD26 inhibitor for less than 2 hours. In certain aspects, the cell population is contacted with said CD26 inhibitor for less than 1 hour.

In certain aspects, the inhibitor is administered in a concentration of less than about 1 nM, about 1, μM, about 5, μM, about 10, μM, about 50, μM, about 100, μM, about 1 mM or about 5 mM. In certain aspects, the inhibitor is administered in a concentration of no less than about 5 mM.

In certain aspects, at least 1 donor cell is treated. In selected embodiments, at least $1\times10^2$, $1\times10^3$, $1\times10^4$, $1\times10^5$, $1\times10^6$, $1\times10^2$, $1\times10^8$ donor cells per mL are treated.

In certain aspects the recipient can be treated with CD26 inhibitor simultaneous with injection of cell surface modified cells. In certain aspects the recipient can be treated with CD26 inhibitor prior to injection of cell surface modified cells. In certain aspects the recipient is pretreated with single or multiple doses of the CD26 inhibitor either simultaneous or prior to cell injection to achieve sustained inhibition of either or both administered cells and recipient CD26 activity leading to enhanced homing of administered cells.

Therapeutic Cell Populations

Stem Cells. In certain aspects, the cell population comprises or consists essentially of a population of stem cells. In certain aspects, the stem cells are selected from a group consisting of: embryonic stem cells, cord blood stem cells, placental stem cells, bone marrow stem cells, amniotic fluid stem cells, hematopoietic stem cells, mesenchymal stem cells, neuronal stem cells, cardiomyocyte stem cells, circulating and immobilized peripheral blood stem cells, mesenchymal stem cells, germinal stem cells, adipose tissue derived stem cells, exfoliated teeth derived stem cells, hair follicle stem cells, dermal stem cells, parthenogenically derived stem cells, reprogrammed stem cells such as induced pluripotent stem cells or somatic nuclear transfer and side population stem cells or transdifferentiated cells. In certain aspects, the embryonic stem cells are totipotent.

As used herein, a "mesenchymal cell" means a cell forming a mesenchymal tissue, such as osteoblast, chondrocyte, myoblast, adipocyte, stroma cell, tendon cell, and the like, a mesenchymal stem cell capable of differentiating into these cells, and its premesenchymal stem cell. Mesenchymal cells generated during the embryo development, mesenchymal cells within an animal body, and mesenchymal cells differentiated and generated from pluripotent stem cells in vitro or in vivo are all encompassed in the term "mesenchymal cell."

As used herein, a "mesenchymal stem cell" means a mesenchymal cell possessing the ability of differentiating into mesenchymal cells of one or more types and the ability of self-replication. The mesenchymal stern cell differentiated from a pluripotent stern cell in vitro is positive for PDGFRα and negative for FLK1. Mesenchymal stem cells are able to differentiate into osteoblasts, chondrocytes, myoblasts, adipocytes, stroma cells, tendon cells, and the like, as with mesodermal cells.

As used herein, a "premesenchymal stem cell" means a mesenchymal cell possessing the ability of differentiating into mesenchymal stern cells of one or more types and the ability of self-replication. The premesenchymal stern cell differentiated from a pluripotent stem cell in vitro expresses Sox1, a neuroectodermal marker. The premesenchymal stem cell is able to differentiate into a mesenchymal stem cell which is PDGFRα-positive and FLK1-negative.

As used herein, a "neural stem cell" refers to a multipotent cell obtained from the central nervous system that can be caused to differentiate into cells that posses one or more biological activities of a neuronal cell type. Neural stem cells differentiate into neurons, astrocytes, and oligodendrocytes after plating onto substrates which stimulate adhesion and differentiation, for example poly-L-ornithine orlaminin. In addition, these multipotent CNS stem cells proliferate and expand in response to epidermal growth factor ("EGF") and basic fibroblast growth factor ("bFGF") and differentiate into neurons, astrocytes, oligodendrocytes, and muscle stem cells.

Committed Progenitor Cells and Differentiated Cells

In certain aspects, the cell population comprises or consists essentially of a population of committed progenitor cells or differentiated cells or transdifferentiated cells. In certain aspects, the cell population is a mature blood cell population. In certain aspects, the mature blood cell is selected from the group consisting of: neutrophils, macrophages and T-cells. In certain aspects, the T-cells are from a heterogeneous population of T-cells.

Patients in Need of Treatment with Modified Cell Populations

In certain aspects, the patient in need of treatment with a cell population suffers from a condition selected from the group consisting of: an acute leukemia, a chronic leukemia, a myelodysplastic syndrome, a stem cell disorder, a myeloproliferative disorder, a lymphoproliferative disorder, a phagocyte disorder, a histiocytic disorder, a lysosomal storage disease, a congenital immune system disorder, an inherited erythrocyte abnormality, an inherited platelet abnormality, a plasma cell disorder, a tumor and an autoimmune disease. In certain aspects, the patient in need of treatment with a cell population suffers from a condition selected from the group consisting of: peripheral arterial diseases, ischemic limb injury, diabetes, heart disease, liver disease, bone disease, muscular dystrophy, Alzheimer's disease, ALS, multiple sclerosis, Parkinson's disease, spinal cord injury, stroke and infertility. Further examples of the above-described conditions are set forth in Table I below.

TABLE I

| Acute Leukemias | Chronic Leukemias |
|---|---|
| Acute Biphenotypic Leukemia | Chronic Lymphocytic Leukemia (CLL) |
| Acute Lymphocytic Leukemia (ALL) | Chronic Myelogenous Leukemia (CML) |
| Acute Myelogenous Leukemia (AML) | Juvenile Chronic Myelogenous Leukemia (JCML) |
| Acute Undifferentiated Leukemia | Juvenile Myelomonocytic Leukemia (JMML) |
| Myelodysplastic Syndromes | Stem Cell Disorders |
| Amyloidosis | Aplastic Anemia (Severe) |
| Chronic Myelomonocytic Leukemia (CMML) | Congenital Cytopenia |
| Refractory Anemia (RA) | Dyskeratosis Congenita |
| Refractory Anemia with Excess Blasts (RAEB) | Fanconi Anemia |
| Refractory Anemia with Excess Blasts in Transformation (RAEB-T) | Paroxysmal Nocturnal Hemoglobinuria (PNH) |
| Refractory Anemia with Ringed Sideroblasts (RARS) | |
| Myeloproliferative Disorders | Lymphoproliferative Disorders |
| Acute Myelofibrosis | Hodgkin's Disease |
| Agnogenic Myeloid Metaplasia (Myelofibrosis) | Non-Hodgkin's Lymphoma |
| Essential Thrombocythemia | Prolymphocytic Leukemia |
| Polycythemia Vera | |
| Phagocyte Disorders | Histiocytic Disorders |
| Chediak-Higashi Syndrome | Familial Erythrophagocytic Lymphohistiocytosis |
| Chronic Granulomatous Disease | Hemophagocytosis |
| Neutrophil Actin Deficiency | Histiocytosis-X |
| Reticular Dysgenesis | Langerhans' Cell Histiocytosis |
| Liposomal Storage Diseases | Congenital (Inherited) Immune System Disorders |
| Adrenoleukodystrophy | Absence of T and B Cells SCID |
| Alpha Mannosidosis | Absence of T Cells, Normal B Cell SCID |
| Gaucher's Disease | Ataxia-Telangiectasia |
| Hunter's Syndrome (MPS-II) | Bare Lymphocyte Syndrome |
| Hurler's Syndrome (MPS-IH) | Common Variable Immunodeficiency |
| Krabbe Disease | DiGeorge Syndrome |
| Maroteaux-Lamy Syndrome (MPS-VI) | Kostmann Syndrome |
| Metachromatic Leukodystrophy | Leukocyte Adhesion Deficiency |
| Morquio Syndrome (MPS-IV) | Omenn's Syndrome |
| Mucolipidosis II (I-cell Disease) | Severe Combined Immunodeficiency (SCID) |
| Mucopolysaccharidoses (MPS) | SCID with Adenosine Deaminase Deficiency |
| Niemann-Pick Disease | Wiskott-Aldrich Syndrome |
| Sanfilippo Syndrome (MPS-III) | X-Linked Lymphoproliferative Disorder |
| Scheie Syndrome (MPS-IS) | |
| Sly Syndrome, Beta-Glucuronidase Deficiency (MPS-VII) | |
| Wolman Disease | |
| Inherited Erythrocyte Abnormalities | Other Inherited Disorders |
| Beta Thalassemia Major | Cartilage-Hair Hypoplasia |
| Blackfan-Diamond Anemia | Ceroid Lipofuscinosis |
| Pure Red Cell Aplasia | Congenital Erythropoietic Porphyria |
| Sickle Cell Disease | Glanzmann Thrombasthenia |
| | Lesch-Nyhan Syndrome |
| | Osteopetrosis |
| | Sandhoff Disease |
| Inherited Platelet Abnormalities | Plasma Cell Disorders |
| Amegakaryocytosis/Congenital Thrombocytopenia | Multiple Myeloma |
| | Plasma Cell Leukemia |
| | Waldenstrom's Macroglobulinemia |
| Other Malignancies | Autoimmune Diseases |
| Brain Tumors | Multiple Sclerosis |
| Ewing Sarcoma | Rheumatoid Arthritis |
| Neuroblastoma | Systemic Lupus Erythematosus |
| Ovarian Cancer | Diabetes Mellitus |
| Renal Cell Carcinoma | Inflammatory Bowel Diseases |
| Small-Cell Lung Cancer | |
| Testicular Cancer | |
| Other Applications | |
| Bone Marrow Transplants | |
| Heart Disease (myocardial infarction), either alone or in | |

TABLE I-continued combination with enhancing agents such as erythropoietin
Liver Disease
Muscular Dystrophy
Alzheimer's Disease
Parkinson's Disease
Spinal Cord Injury
Stroke, either alone or in combination with enhancing agents
such as erythropoietin
Peripheral Vascular Disease
Head trauma
Ex vivo and In vivo expanded stem and progenitor cell
populations
In vitro fertilization application and enhancement
Hematopoietic Rescue Situations (Intense Chemo/Radiation)
Stem cells and progenitor cells derived from various tissues
sources
Application in humans and animals
Limb regeneration, alone or in combination with enhancing
agents Cell therapy is also desirable for treatment of diseases in which the immune system is sought to be enhanced. One particular form of cell therapy involves the expansion of T cells that possess specificity for a distinct antigen, for example a tumor antigen. In other types of cell therapy, T cells are generated, and reprogrammed ex vivo for ability to kill a plurality of cells that express a plurality of markers. Examples of such cell therapy include expansion of autologous T cells with IL-2, stimulation with tumor cell lysates, and reintroduction of said cells into the patient.

On the other hand, cell therapy may be performed in situations where suppression of an immune response is desired. In such situations expansion of cells such as CD4+ CD25+ regulatory T cells is desirable since these cells are capable of inhibiting immune responses in an antigen-specific manner. Methods for expansion of these cells are commonly known and include use of cytokines such as TGF-b.

One issue in bone marrow homing is that the receptors on endothelial cells for the glycosylated ligands of circulating cells are constitutively expressed. These receptors, such as P and E selectins, induce numerous activities after interacting with cells, including causing apoptosis or proliferative arrest (Winkler et al., Blood 2004 103: 1685-1692). Accordingly, the administration of hematopoietic cells and their subsequent homing to the bone marrow is dependent on molecules that are consitutively expressed.

For the purpose of a broader application of this approach for regenerative medicine in which cells are administered for non-hematopoietic purposes, the trafficking/homing of cells to the targeted location is much more complex and involves ligands that are not constitutively expressed, but expressed as a result of inflammation or tissue damage. For example, administration of stem cells for the purpose of treating myocardial infarction depends on homing of these cells to areas bathed in cytokine locally released which not only induces expression of E selectin and P selectin on the endothelium but also mediates chemoattraction to the site. This tissue localized upregulation of receptors and chemoattractant agents allows for homing of stem cells into areas of injury.

Routes of Administration

Administration of the modified cells is performed in agreement with standard practices that are known to one skilled in the art. Several embodiments are possible. For example, routes of administration may include parenteral, e.g., intravenous, intradermal, microvascular bed of bone marrow, subcutaneous, oral (e.g., ingestion or inhalation), trans dermal (topical), transmucosal, and rectal administration. In certain particular aspects, the population of modified cells is administered from a route selected from a group consisting of: intravenously, intraarterially, intramuscularly, subcutaneously, transdermally, intratracheally, intraperitoneally, intravitreally, via direct injection, into bone compartments or into spinal fluid. In some aspects the cells, compositions or other materials can be used with a scaffolding support. In certain aspects, the population of modified cells is administered in or proximal to a site of injury. In certain aspects, the homing and engraftment takes place within the bone marrow of the patient in need thereof. In certain aspects, the cells are administered by multiple routes and/or sites, either simultaneously or sequentially.

In another embodiment, the methods, compositions, cells and other materials can be useful for enhancing functional capabilities in a wide variety of not only hematological disorders but also non-hematological disorders. Specifically, the methods, compositions, cells and other materials may be useful for the treatment of medical conditions which are amenable to cell therapy. More specifically, the methods, compositions, cells and other materials may be useful for the treatment of acute leukemias, chronic leukemias, myelodysplastic syndromes, stem cell disorders, myeloproliferative disorders, lymphoproliferative disorders, phagocyte disorders, histiocytic disorders, lysosomal storage diseases, congenital immune system disorders, inherited erythrocyte abnormalities, other inherited disorders, inherited platelet abnormalities, plasma cell disorder, various malignancies such as brain tumors or Ewing sarcoma, Autoimmune Diseases, and other applications such as bone marrow transplants, diabetes, heart disease, liver disease, hematopoietic rescue situations following intense chemo/radiation, limb ischemia and limb regeneration (including cartilage regeneration, skin regeneration, blood vessel regeneration, etc), cartilage regeneration, skin regeneration, blood vessel regeneration, etc.

Furthermore, presented herein is the finding that the general increased adhesion of cells that have been fucosylated ex vivo can be utilized for augmented binding to localized niche areas in absence of chemotactic gradient such as in the context of portal vein injection or pulmonary artery injection.

For P-selectin binding cells can be incubated with anti-CD34+-PE and with P-selectin isolated from human platelets. P-selectin binding can be detected with FITC-labeled S12, a non-blocking mAb to human P-selectin. For E-selectin binding cells can be incubated with E-selectin/IgM after Fc receptor blocking. E-selectin can then be detected with FITC-labeled goat anti-human IgM polyclonal antibodies. Visualization of binding can be achieved using FACS analysis. Incubation for both P and E-selectin can be carried out at 4° C. for 20 minutes.

To confirm a functional consequence of fucosylation following treatment with fucosyltransferase the cells can be examined for adhesion to either E-selectin or P-selectin under physiological shear forces using an in vitro flow chamber rolling assay system. P-selectin isolated from human platelets can be immobilized on plates in a parallel-plate flow chamber. A P-selectin site density of about 145 sites/$\mu m^2$ can be used and measured by binding of $^{125}$I-labeled anti-P-selectin mAb S12. For E-selectin soluble human E-selectin can also be immobilized on plates in a parallel-plate flow chamber at a density of 200 sites/$\mu m^2$, as measured by binding of $^{125}$I-labeled anti-human E-selectin mAb ES1. Sham-treated or FTVI-treated cells (in Hanks' balanced salt solution and 0.5% human albumin) can be perfused over P- or E-selectin coated plates at a wall shear stress of 1 dyn/$cm^2$. The accumulated number of rolling cells can be measured with the aid of a videomicroscopy system coupled to an image analysis system. Specificity of interaction of cells with the coated plates can be confirmed with the inclusion of specific inhibitors to the binding and examination of rolling on plates coated only with human serum albumin.

EXAMPLES

Examples are provided hereinbelow. However, the presently disclosed and claimed inventive concept(s) is to be understood to not be limited in its application to the specific experimentation, results and laboratory procedures. Rather, the Examples are simply provided as one of various embodiments and are meant to be exemplary, not exhaustive.

Example 1

Parameters for Maximal FTVI Activity in Cord Blood

Enzymatic-mediated fucosylation ($\alpha$ 1-3-linked fucose addition to cell-surface glycans) has shown both phenotypic and functional changes in MNC and $CD3^+$ cell populations.

These in vitro studies are structured to examine the various components integral to the enzymatic-mediated fucosylation using a cell preparation procedure routinely practiced in the clinic. A frozen thawed human cord blood mononuclear cell population is washed by a procedure that involves a 1 to 10 dilution with chilled 10% Dextran-40/5% HSA solution, placing this diluted solution in a pre-cooled (2-6° C.) centrifuge for 5-10 minutes followed by mild centrifugation at approximately 550 g for 20 minutes. The supernatant is discarded while the pellet is resuspended in Hank's balanced salt solution (HBSS) containing 1% HSA at a target cell concentration ranging from $0.5 \times 10^6$ to $1 \times 10^9$ per ml. This cell population suspended in fucosyltransferase VI (FTVI) reaction media constitutes the core preparation used to examine a range of various parameters in order to identify the optimal conditions for maximal activity of FTVI within this cell population. The parameters examined are Mn++ (over final concentration ranging from 0.0 to 10 mM), GDP-fucose (over final concentration ranging from 0.3 to 10 mM), time course analysis with varying periods of incubation (ranging from 15 minutes to 60 minutes), FTVI (over a 20 fold range of enzyme concentration), temperature [10° C., 25° C. (considered as room temperature) and 37° C.] and cell concentration (over final concentration ranging from $0.5 \times 10^6$ to $1 \times 10^9$ per ml). Additional activities within these optimization efforts include assessing the stability of the fucosylated product with an examination of HECA-452 binding at 30, 60, 120, 180 and 240 minutes post termination of reaction and assessing the extent of fucosylation of additional cell populations. The cell preparation in reaction mix is incubated for 30 minutes (except for time course study) with occasional gently mixing. The solutions are then diluted with cold HBSS 1% HSA, filtered through 70 micron cell screen and subjected to chilled centrifugation for 12 minutes. The supernatant is discarded, pellet loosened and resuspended for either injection or analysis by FACS using a procedure that is familiar to someone skilled in the art. For FACS analysis, aliquots of the cells, at approximately $5 \times 10^5$, are centrifuged at 500×g for 13 minutes at 4° C. The supernatant is discarded, pellet loosened for the addition of flow stain cocktail containing the appropriate staints) or control cocktail. The mixture is stored in the dark for 30-40 minutes with occasional mixing. Each tube is diluted with 3 ml of cold flow wash buffer followed by centrifugation at 500×g for 12 minutes at 4° C. The supernatant is discarded, pellet loosened with the addition of approximately 200 µl of cold flow buffer or flow fix buffer. Aliquots of each sample are examined by FACS for percentage of double positives for $CD34^+$ vs HECA-452 which is the primary outcome measure for determining maximal expression of FTVI activity in the cell mix. Also generated as an outcome measure for assessment of enzyme activity is the mean fluorescence intensity

Example 2

Enhanced Engraftment in the Bone Marrow Using q Combination Approach Consisting of Maximal Fucosylation of Cell Preparation Plus Exposue to a CD26 Inhibitor First, maximal fucosylation of cells in vitro is accomplished. To accomplish this, washed mononuclear cells (MNCs) are resuspended in Hank's Balanced Salt Solution (HBSS) at a concentration of $0.5 \times 10^6$-$1 \times 10^9$ per ml and then incubated with a fucosylation mix consisting at final concentration of 5 mM GDP-fucose, purified human recombinant $\alpha$1-3 fucosyltransferase VI at a predetermined Units per ml (for maximal fucosylation), and 1-10 mM $MnCL_2$ in HBSS. This mix is incubated for 30 minutes at 37° C. or room temperature in a humidified atmosphere containing 5% $CO_2$. The period of incubation could take longer or shorter depending on the incubation temperature chosen. Following completion of the fucosylation and to achieve inhibition of CD26 (dipeptidylpeptidase, DPPIV) as part of the combination approach, this preparation of fucosylated mononuclear cells (MNCs) is either washed first or directly incubated with a potent DPPIV inhibitor for 5-15 minutes at room temperature at a concentration sufficient to achieve complete or nearly complete inhibition of DPPIV. Following incubation the cell suspension is volume adjusted with HBSS or another clinically compatible solution to obtain the appropriate concentration of cells in preparation for iv injection. As an alternative scenario for a combination approach, the patients are subjected to systemic administration of the DPPIV inhibitor at a dose sufficient to achieve a sustained level in the body for significant inhibition of bone marrow and circulating plasma DPPIV activity. Subsequent to systemic pretreatment, MNCs exposed to conditions for maximal fucosylation are then injected into the patient. The DPPIV inhibitor can be added simultaneous with the injection of the fucosylated cell preparation or shortly before. The patients are prepared for this combined approach by subjecting them to conditions for myeloablation or even partial myeloablation (mini) prior to injection of the fucosylated and inhibitor treated cells. The rate of recovery and extent of chimerism is assessed with an examination of serially collected blood samples in addition to an examination of cells obtained from the bone marrow. A multilineage analysis of the rate of recovery and extent of engraftment and chimerism is accomplished using cell surface markers specific for cell types in addition to an examination of mature hematopoietic cells in the blood stream. These markers and cells are detected using preparation techniques and FACS analysis procedures that are familiar to one skilled in the art.

Example 3

Ex Vivo Fucosylation of Mesenchymal Stem Cells

The introduction of fucose onto surface glycans of mesenchymal stem cells (MSC) is accomplished by enzymatic transfer from a donor substrate utilizing an alpha 1-3-fucosyltransferase (FT). For this transfer to occur the cells at varying concentrations are exposed to an incubation buffer containing a number of ingredients each of which has been optimized for efficient transfer of the fucose, and performed in Hanks balanced salt solution (HBSS). The substrate, guanosine diphosphate-fucose (GDP-fucose), at 1 mM is mixed with the FT added at sufficient activity, in order to achieve maximal transfer of fucose to MSCs. In addition, MrrCl, at a final concentration of 0-10 mM is added, as needed, to further accelerate the enzymatic transfer reaction. The incubation is performed at 37° C. for 40 minutes with minimum toxicity to the cells.

Confirmation of fucosylated epitopes on the cells of interest as means of confirming maximal levels of fucosylation is verified by Flow Cytometry in order to detect sialyl LewisX (sLeX), a fucosylation epitope found on both P and E-selectins. The FT-treated cells are incubated with anti-sLeX mAb HECA 452 (IgM), followed by treatment with FITC-conjugated fragment to the IgM. Finally, the sLeX epitopes on the cell surface are visualized using standard Flow Cytometry procedures.

To measure P-selectin binding, cells are incubated with anti-CD34$^+$-PE and with P-selectin isolated from human platelets. P-selectin binding is detected with FITC-labeled S12, a non-blocking mAb to human P-selectin. To measure E-selectin binding, cells are incubated with E-selectin/IgM after Fe receptor blocking. E-selectin is then detected with FITC-labeled goat anti-human IgM polyclonal antibodies. Visualization of binding is achieved using FACS analysis. Incubation for both P and E-selectin is carried out at 4° C. for 20 minutes.

To confirm a functional consequence of fucosylation following treatment with FT the cells are examined for adhesion to either E-selectin or P-selectin under physiological shear forces using an in vitro flow chamber rolling assay system. P-selectin isolated from human platelets is immobilized on plates in a parallel-plate flow chamber. A P-selectin site density of about 145 sites/$\mu m^2$ is used and measured by binding of $^{125}$I-labeled anti-P-selectin mAb S12. For E-selectin soluble human E-selectin is also immobilized on plates in a parallel-plate flow chamber at a density of 200 sites/$\mu m^2$ as measured by binding of $^{125}$I-labeled anti-human E-selectin mAb ES1. Sham-treated or FTVI-treated cells (in Hanks' balanced salt solution and 0.5% human albumin) is perfused over P- or E-selectin coated plates at a wall shear stress of 1 dyn/$cm^2$. The accumulated number of rolling cells is measured with the aid of a videomicroscopy system coupled to an image analysis system. Specificity of interaction of cells with the coated plates is then confirmed with the inclusion of specific inhibitors to the binding and examination of rolling on plates coated only with human serum albumin.

Example 4

Administration of Modified Stem Cells to Bone Marrow Transplant Patients

Patients in need of a bone marrow transplant are subjected to either myeloablative or non-myeloablative conditions. Stem cells obtained from one of a number of different sources are incubated ex vivo with fucosyltransferase+GDP-fucose at sufficient concentrations and for a sufficient period of time to result in maximal formation of fucosylated product, such as sialyl Lewis X, on the cell surface. Following treatment, the cell preparation is washed or directly injected into the patient. Effectiveness of this application in the patient is determined with accelerated appearance over time of neutrophils and platelets in the blood stream compared to patients injected with control untreated stem cells.

Example 5

Modification of Neural Stem Cells

A cell population consisting of neural stem cells is treated with conditions so as to endow increased surface ligands for enhanced interaction with endothelium. Cells are modified with the addition of alpha 1-3-linked fucose to cell-surface glycans by ex vivo treatment of cells with the enzyme alpha 1-2 fucosyltransferase VI. Specifically, cells are treated with 1 mM GDP fucose, 20 mU/mL {alpha}1-3 fucosyltransferase VI, and 10 mM MnCl2 in 0.5 mL HBSS containing 1% human serum albumin (HSA) for 30 minutes at 37° C. in a humidified atmosphere containing 5% $CO_2$ under conditions that cause minimum toxicity to CD34$^+$ cells as tested by propidium iodide staining measured by flow cytometry. Other modifications of this treatment procedure may be performed based on the knowledge of one skilled in the art. Said treated neural stem cells are subsequently assessed for fucosylation using flow cytometric methodology. The cells are placed on ice for 5 minutes followed by washing with PBS (1 ml). To detect the presence of new fucosylated units on cell surface the cell preparation is treated with the 1$^{st}$ antibody, anti-CLA 1:200 dilution in blocking buffer (400 µl), and then incubated for one hour at room temp or overnight at 4°. Cells are then washed three times with PBS. The secondary antibody (anti-rat-IgM-PE, 1:200) in blocking buffer (400 µl) is then added. The preparation is incubated for 2 hrs at room temperature then rinsed with PBS. The result of this treatment and analysis is shown in FIG. 1.

Example 6

Modification of Immune Modulatory Cells

A cell population consisting of cells with immune modulatory potential is treated with certain conditions so as to endow increased surface ligands for endothelium. Cells are modified with alpha 1-3-linked fucose to cell-surface glycans by treatment of cells with the enzyme alpha 1-2 fucosyltransferase VI. Specifically, cells are diluted to a concentration of 10(7) per ml and treated with 1 mM GDP fucose (EMD Bioscienees, San Diego, CA), 20 mU/mL {alpha} 1-3 fucosyltransferase VI (FTVI; EMD Biosciences), and 10 mM $MnCl_2$ in 0.5 mL HBSS containing 1% human serum albumin (HSA) for 30 minutes at 37° C. in a humidified atmosphere containing 5% $CO_2$ under conditions that cause minimum toxicity to $CD34^+$ cells as tested by propidium iodide staining measured by flow cytometry. Other modifications of this treatment procedure may be performed based on the knowledge of one skilled in the art. Said treated immune cells are subsequently assessed for fucosylation status using either a flow cytometrie methodology (assessment of HECA-453 binding) or functional methodology (assessment of rolling on endothelium). Cells are subsequently administered to a patient for immune modulation.

Example 7

Augmenting Efficacy of Tumor Infiltrating Lymphocytes After Ex Vivo Expansion

Tumor infiltrating lymphocytes were collected as described by Zhou et al *The Journal of Immunology*, 2005, 175: 7046-7052. Briefly, explants of small (2 mm3) tumor fragments or $1 \times 10^6$ viable cells of tumor tissue digests were used to initiate TIL culture in 2 ml of RPMI 1640-based medium (Invitrogen Life Technologies) containing 10% human serum and 6000 IU/ml IL-2 (Chiron). After 2-4 weeks of culture, several million TIL cells were usually obtained and screened by IFN secretion assay for recognition of tumor cells. Antitumor TIL cultures were further expanded in AIM V medium (Invitrogen Life Technologies) supplemented with irradiated allogeneic feeder cells, anti-CD3 Ab (Ortho Biotech), and 6000 IU/ml IL-2. This expansion protocol typically resulted in 1000-fold expansions of cells by the time of administration 14-15 days after initiation of the expansions. Subsequent to expansion cells were harvested, centrifuged, diluted to a concentration of 10(7) per ml, and treated with 1 mM GDP fucose (EMD Biosciences, San Diego, CA), 20 mU/mL alpha 1-3 fucosyltransferase VI (FTVI; EMD Biosciences), and 10 mM $MnCl_2$ in 0.5 mL HBSS containing 1% human serum albumin (HSA) for 30 minutes at 37° C. in a humidified atmosphere containing 5% $CO_2$ under conditions that cause minimum toxicity to cells, as tested by propidium iodide staining measured by flow cytometry. Cells were administered on a weekly basis at a concentration of at least about 1 million cells, but in some situations up to 100 million cells, over a period of 60-120 minutes. After four cycles of therapy, tumor regression was noted.

Example 8

Ex Vivo Fucosylation OF T Cells

In order to compare the effects of ex vivo fucosylation on different T cell types, recombinant FTVI produced in CHO cells was manufactured at Aragen Bioscience (Morgan Hill, CA, final concentration 1100 ug/mL), and FTVII produced in a mouse lymphocyte line was obtained from Kyowa Hakko Kirin (Japan, final concentration 150 ug/mL). Frozen human umbilical cord bloods were purchased from the San Diego Blood Bank (San Diego, CA). Unless otherwise indicated, cells were treated at $10^6$ cells/ml for 30 minutes at room temperature with 1 mM GDP β-fucose (EMD Biosciences, San Diego, CA) in Phosphate Buffered Saline (PBS) containing 1% human serum albumin (HSA, Baxter Healthcare Corp., Westlake Village, CA) and in the presence of previously optimized concentrations of FTVI (100 mU/ml) or FTVII (75 μg/ml). The FTVI+GDP-fucose is referred to herein as TZ101 (previously referred to as ASC-101; Targazyme, Inc., Carlsbad, CA), while the FTVII+GDP-fucose composition is referred to herein as TZ102 (previously referred to as ASC-102; Targazyme, Inc., Carlsbad, CA). Untreated cells were incubated as above, except that no enzyme was added. Fucosylation levels were determined by flow cytometry using HECA-452 antibody (BD Biosciences, San Jose, CA), a directly conjugated (FITC), rat IgM antibody that reacts against a fucosylated (sialyl Lewis X (sLeX)-modified) form of P-selectin glycoprotein ligand (PSGL)-1 (CD162), also known as cutaneous lymphocyte antigen (CLA). Other antibodies to CD antigens were also obtained from BD Biosciences.

Regulatory T Cells

Figure 2:
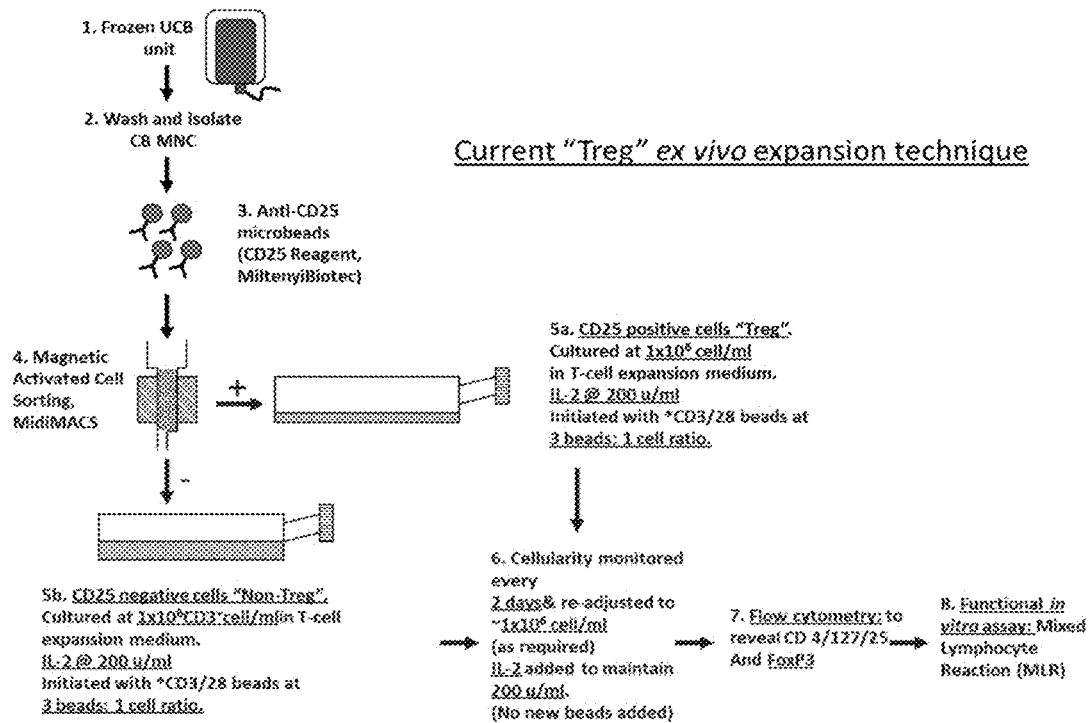
FIG. 2 graphically depicts the ex vivo expansion technique utilized herein for T cells.

Regulatory T cells ("Tregs") were enriched from cord blood using magnetic bead-isolation (using MACS® beads, Miltenyi Biotec Inc., San Diego, CA) for $CD25^+$ cells and expansion of Tregs with IL-2 and CD3/28 beads, as shown in FIG. 2.

Figure 3:
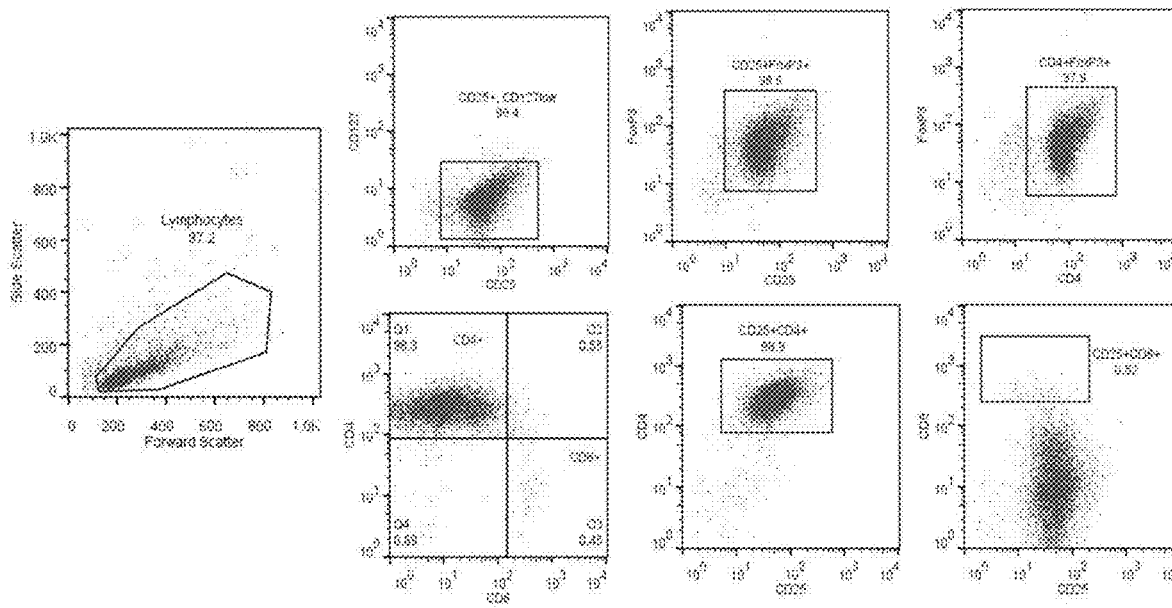
FIG. 3 contains a flow cytometry analysis of expanded Regulatory T cells (Tregs).

FIG. 3 demonstrates a flow cytometry analysis of Tregs expanded in this manner. As shown in the upper right hand panels (left to right) of FIG. 3, 97.2% of cells are within the lymphocyte gate, while 98.4% express Treg markers CD25/CD127. As shown in the lower panels (left to right) of FIG. 3, 98.6% of cells are $CD25^+FoxP3^+$; 97.9% are $CD4^+FoxP3^+$; 98.9% of cells are $CD25^+CD4^+$; and 0.52% of cells are $CD25^+CD8^+$.

Figure 4:
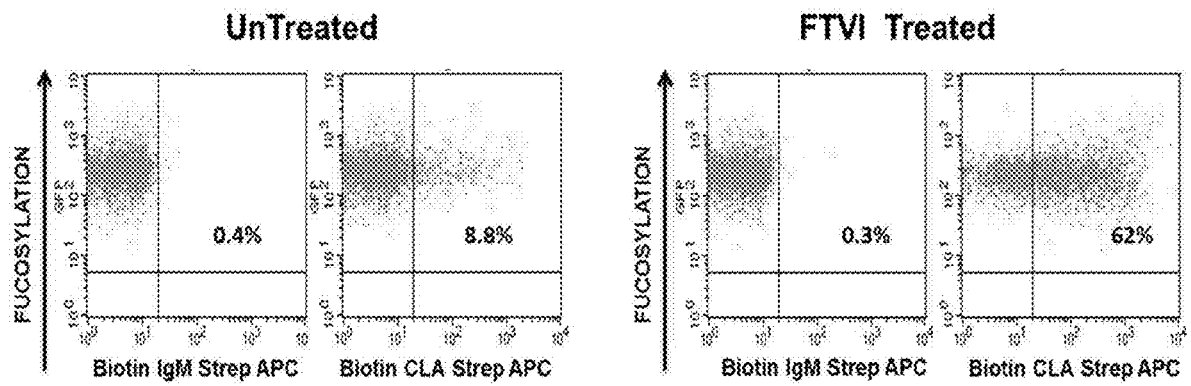
FIG. 4 contains a flow cytometry analysis of Tregs fucosylated with TZ101 (FTVI+GDP-fucose; Targazyme, Inc., Carlsbad, CA).

Tregs were fucosylated with TZ101 (1/25 dilution of TZ101 in 1 mM GDP-Fucose, PBS 1% human serum albumin) for 30 minutes at room temperature, washed, and assayed for cell surface expression of sialyl Lewis X (sLeX) using the HECA 452 anti-CLA antibody. The left side of each dot plot of FIG. 4 shows the isotype control, while the right side shows the staining with percent CLA positive cells. As shown in FIG. 4, treatment with TZ101 increased the percentage of fucosylated Tregs from about 9% to about 63%.

Figure 5:
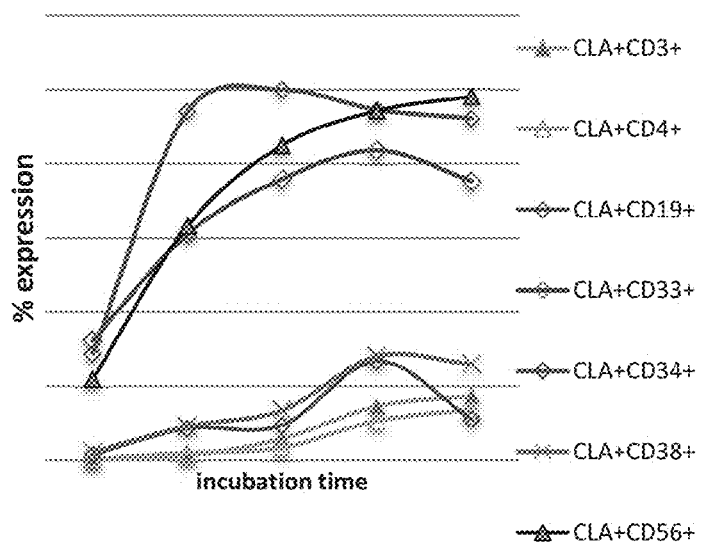
FIG. 5 graphically illustrates the ability of TZ101 to fucosylate various types of cells.

As shown in FIG. 5, the ability to fucosylate ex vivo expanded Tregs is unexpected in light of previous studies showing that TZ101 fucosylated $CD34^+$ (red curve), $CD33^+$ (blue curve), and $CD56^+$ cells (black curve) at different time points but did not fucosylate CD3 positive T cells in unexpanded cord blood (green curve).

A xenogeneic graft-versus-host (GVHD) model was developed in which NOD/SCID IL-2R$\gamma^{null}$ (NSG) mice (Jackson Laboratory, Bar Harbor, ME) received sub-lethal whole body irradiation (300 cGy from a $^{137}$Cs source delivered over one minute by a J. L. Shepherd and Associates Mark I-25 Irradiator, San Fernando, CA) one day prior (Day-1) to intravenous infusion of human peripheral blood mononuclear cells (PBMC). On Day-0, mice received PBMC at a dose of $1 \times 10^7$.

Figure 6:
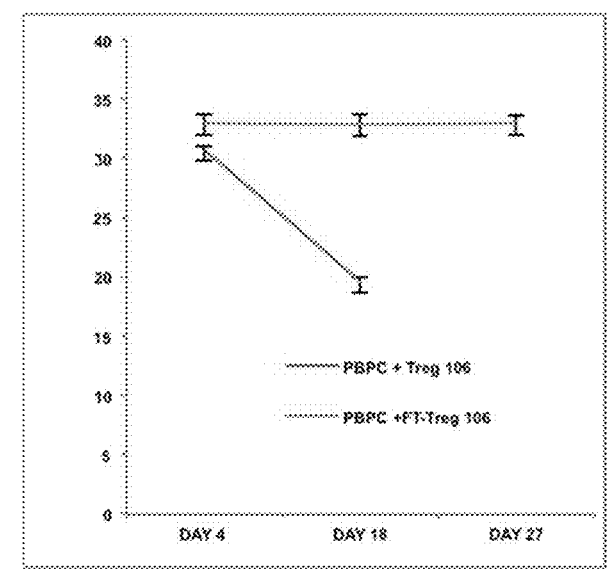
FIG. 6 graphically illustrates the ability of fucosylated Tregs to prevent graft-versus-host disease (GVHD) in a mouse model.

As shown in FIG. 6, fucosylated Tregs prevented development of GVHD, while unmanipulated Tregs did not. Sublethally irradiated NSG mice received Treg or FT-Treg at a cell dose of $1 \times 10^6$ on Day-1 followed by tail vein injection of PBMC at cell dose of $1 \times 10^7$ on Day-0. The mice were followed for survival and weight. All the Treg recipients were dead at Day-20; however, the FT-Treg recipients were alive at the last follow up. While the Treg recipients started losing weight as early as Day-12, FT-Treg recipients maintained their weight until their last follow up.

Cytotoxic T Cells

Surprisingly, in contrast to Tregs, expanded CD8+ T cells were not fucosylated by TZ101 (FTVI+GDP-fucose) but were fucosylated by TZ102 (FTVII+GDP-fucose).

In order to generate cytotoxic T cells that were capable of killing acute myelogenous leukemia (AML) cells, dendritic cells (DC) were generated from HLA-A*0201 healthy donor monocytes by adherence and matured and subsequently used as antigen presenting cells (APC). Healthy donor PBMCs were adhered on 6-well plates at 37oC in serum-free medium. Cells remaining in suspension (lymphocytes) from the same donor were removed and pulsed with 40 μg/mL of a peptide (CG1) derived from the myeloid primary granule protease (PGP) cathepsin G (CG) that has been established as a myeloid leukemia target. A separate incubation was conducted with control peptides. The suspension cells were stimulated with IL-7 (10 ng/mL) and IL-2 (10 ng/mL) for 5 days. Adherent cells from the initial step were matured into monocyte-derived DC by addition of GM-CSF (100 ng/mL), IL-4 (50 ng/mL), and TNF-α (25 ng/mL). After 5 days, DC were detached and pulsed with appropriate peptides at 40 μg/mL and subsequently combined with the remainder of autologous lymphocyte population. Co-cultures were then re-stimulated with IL-7 (10 ng/mL) and IL-2 (25 ng/mL) for 7 days to allow for CTL proliferation. On Day-12, cells were harvested and analyzed by dextramer staining and in vitro cytotoxicity assays to confirm CTL expansion and specificity. Using this method, CG1-CTL (experimental effector cells) as well as CTL that target the HLA-A*0201 HIV Gag (SLYNTVATL) control peptide were generated.

Figure 7:
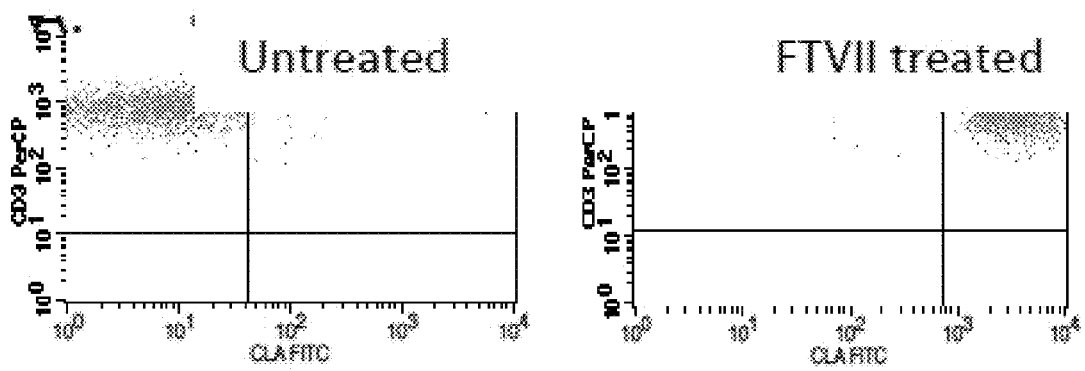
FIG. 7 graphically illustrates the ability of TZ102 (FTVII+GDP-fucose; Targazyme, Inc., Carlsbad, CA) to fucosylate ex vivo expanded cytotoxic T cells (CTL).

As shown FIG. 7, TZ102 (FTVII) was capable of fully fucosylating expanded CTL; however, FTVI did not fucosylate these cells (data not shown).

Figure 8:
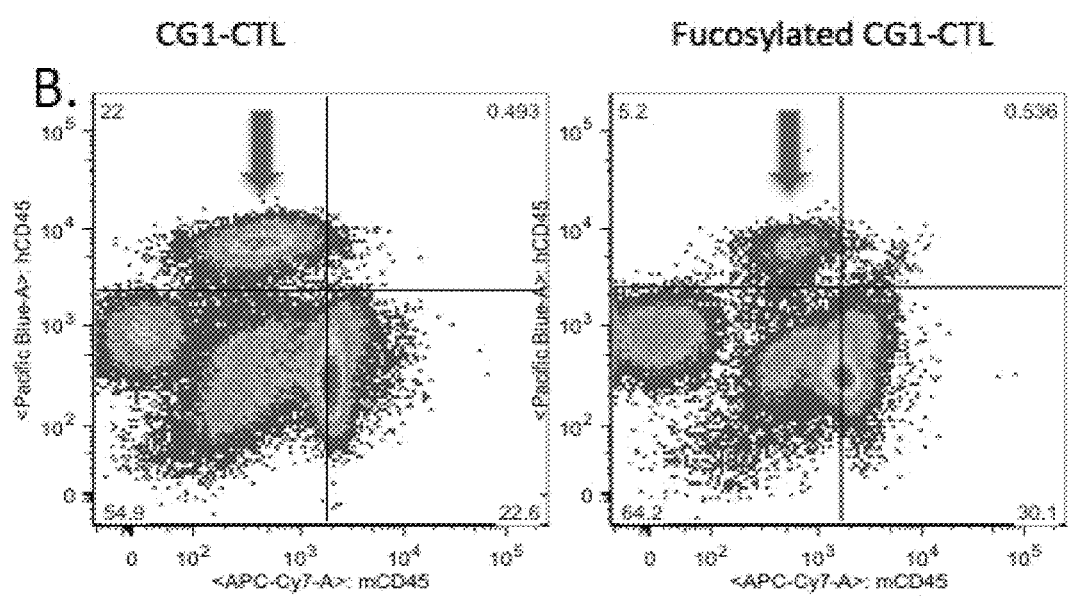
FIG. 8 contains an analysis of the ability of FTVII-treated CTL to kill leukemia cells in a xenogeneic AML mouse model.

In order to compare the efficacy of FTVII-treated CTL to unmanipulated CTL, a xenogeneic AML model was developed. Cells from the human U937 leukemia cell line transduced with HLA-A2 and GFP were administered to NSG mice on Day-0. Cytotoxic T cells were expanded against CG1 as described above. Fucosylated or non-fucosylated T cells were administered to NSG mice with U937 leukemia on Day-1, and bone marrow was harvested 14 days later and assessed for the presence of U937 cells (upper left quadrant of FIG. 8). There were significantly fewer leukemia cells in mice receiving fucosylated T cells (arrows in FIG. 8).

One of ordinary skill in the art will appreciate that these methods, compositions, and cells are and may be adapted to carry out the objectives and obtain the ends and advantages mentioned, as well as those inherent therein. The methods, procedures, and devices described herein are presently representative of particular embodiments and are exemplary and are not intended as limitations on the scope of the technology. Changes therein (including, but not limited to, changes in method steps as well as sequence of method steps) and other uses will occur to those of ordinary skill in the art which are encompassed within the spirit of the technology and are defined by the scope of the disclosure. It will be apparent to one of ordinary skill in the art that varying substitutions and modifications can be used or substituted into any of the embodiments described herein may be made without departing from the scope and spirit of the described technology. Examples of such substitutions are non-natural enzymes and sugars. Those of ordinary skill in the art recognize that the aspects and embodiments set forth herein may be practiced separate from each other or in conjunction with each other. Therefore, combinations of separate embodiments are within the scope of the technology as disclosed herein.

What is claimed is:

1. A method of enhancing homing and engraftment of one or more T cells, the method comprising the step of:
   (i) isolating a T cell population from a blood sample from a patient, wherein the T cell population comprises cytotoxic T cells;
   (ii) expanding the cytotoxic T cells present in the T cell population ex vivo;
   (iii) contacting the T cell population with α1,3-fucosyltransferase VII and a fucose carrier ex vivo to fucosylate at least one surface molecule on the cytotoxic T cells to enhance selectin mediated binding thereof;
   (iv) combining the fucosylated, expanded cytotoxic T cells with a pharmaceutically-acceptable carrier to provide a pharmaceutical composition capable of administration to the patient; and
   (v) administering the pharmaceutical composition to the patient via a route selected from a group comprising intravenously, intraarterially, intramuscularly, subcutaneously, transdermally, intratracheally, intraperitoneally, intravitreally, and combinations thereof.

2. The method of claim 1, wherein the T cell population is further defined as a heterogeneous population of T cells.

3. The method of claim 1, wherein the fucose carrier is mixed with the alpha 1,3-fucosyltransferase VII prior to contacting the mixture with the T cell population, and wherein the fucose carrier is guanosine diphosphate fucose.

4. The method of claim 1, wherein step (iii) is performed in the presence of manganese.

5. The method of claim 1, wherein step (iv) is performed in the presence of human serum albumin.

6. The method of claim 1, further defined as a method of treating or reducing the occurrence of acute myelogenous leukemia.

7. The method of claim 1, wherein in step (v), the pharmaceutical composition is administered to a site of injury or proximal thereto.

* * * * *